United States Patent [19]
Butters et al.

[11] Patent Number: 6,019,788
[45] Date of Patent: Feb. 1, 2000

[54] VASCULAR SHUNT GRAFT AND JUNCTION FOR SAME

[75] Inventors: Leslie C. Butters; Charles E. Biggerstaff; Brian M. Conn; Ramona Hicks, all of Flagstaff; Anita Switzer, Parks, all of Ariz.

[73] Assignee: Gore Enterprise Holdings, Inc., Newark, Del.

[21] Appl. No.: 08/964,119

[22] Filed: Nov. 4, 1997

Related U.S. Application Data

[63] Continuation-in-part of application No. 08/745,672, Nov. 8, 1996, abandoned.

[51] Int. Cl.[7] .................................................. A61F 2/06
[52] U.S. Cl. .................................. 623/1; 623/12; 604/8
[58] Field of Search ................................ 623/1, 2, 3, 9, 623/11, 12; 604/8, 27, 43, 171; 600/36

[56] References Cited

U.S. PATENT DOCUMENTS

| | | | |
|---|---|---|---|
| 2,127,903 | 8/1938 | Bowen | 128/334 |
| 3,042,021 | 7/1962 | Read | 128/1 |
| 3,683,926 | 8/1972 | Suzuki | 128/334 R |
| 4,230,119 | 10/1980 | Blum | 128/325 |
| 4,352,358 | 10/1982 | Angelchik | 128/334 R |

(List continued on next page.)

FOREIGN PATENT DOCUMENTS

| | | |
|---|---|---|
| 1 518 083 | 7/1968 | France . |
| 2666502 | 3/1992 | France ........................ 623/1 |
| 2 000 684 | 1/1979 | United Kingdom . |
| 2269104 | 2/1994 | United Kingdom . |
| 84/03036 | 1/1984 | WIPO . |
| 89/05127 | 6/1989 | WIPO . |

OTHER PUBLICATIONS

Literature: Howard M. Crawshaw, FRCS; William C. Quist; Eugene Serrallach, PhD; C. Robert Valeri, MD; Frank W. LoGerfo, MD, "Flow Disturbance at the Distal End–to–Site Anastomosis," Arch Surg vol. 115, (1980) pp. 1280–1284.

Literature: Philip B. Dobrin, MD, PhD, Fred N. Littooy, MD, and Eric D. Endean, MD, "Mechanical factors predisposing to intimal hyperplasia and medial thickening in autogenous vein grafts," Surgery vol. 106, No. 3 (1989) pp. 393–400.

Literature: Mark F. Fillinger, MD, Emanuel R. Reinitz, MD, Robert A. Schwartz, MD, Dennis E. Resetarits, MD, Andrew M. Paskanik, Carl E. Bredenberg, MD, "Beneficial Effects of Banding on Venous Intimal–Medial Hyperplasia in Arteriovenous Loop Grafts," The American Journal of Surgery vol. 158 (1989) pp. 87–94.

Literature: Mark F. Fillinger, MD, Emaunel R. Reinitz, MD, Robert A. Schwartz, MD, Dennis E. Resetarits, MD, Andrew M. Paskanik, David Bruch, MS, and Carl E. Bredenber, MD, "Graft Geometry and Venous Intimal–Medial Hyperplasia in Arteriovenous Loop Grafts," Journal of Vascular Surgery vol. 11, No. 4, (1990) pp. 556–566.

(List continued on next page.)

*Primary Examiner*—Mickey Yu
*Assistant Examiner*—Tram A. Nguyen
*Attorney, Agent, or Firm*—David J. Johns

[57] ABSTRACT

An improved implantable medical device and junction between a blood conduit and a blood vessel are disclosed. The device of the present invention provides a connection to a blood vessel that is resistant to occlusion. Resistance to occlusion is achieved by providing an implantable medical junction with: improved and consistent anastomotic geometry and hemodynamics to minimize turbulence and inappropriate shear stresses on the native blood vessels; intraluminal configuration that does not require penetration through to the luminal surface of the blood vessel or the device for anchoring; protection of the native blood vessel from the forces of blood flow in the impact zone and beyond the impact zone; and isolation of injured and traumatized tissues from the lumen of the blood vessel and the device. A cuff is also provided at the junction to reduce blood leakage from the native blood vessel, and to provide additional device anchoring.

48 Claims, 16 Drawing Sheets

U.S. PATENT DOCUMENTS

| | | | |
|---|---|---|---|
| 4,366,819 | 1/1983 | Kaster | 128/334 C |
| 4,470,415 | 9/1984 | Wozniak | 128/334 R |
| 4,474,181 | 10/1984 | Schenck | 128/334 R |
| 4,501,263 | 2/1985 | Harbuck | 128/1 R |
| 4,503,568 | 3/1985 | Madras | 3/1.4 |
| 4,512,761 | 4/1985 | Raible | 604/8 |
| 4,593,693 | 6/1986 | Schenck | 128/334 R |
| 4,657,019 | 4/1987 | Walsh et al. | 128/334 C |
| 4,719,916 | 1/1988 | Ravo | 623/12 |
| 4,728,328 | 3/1988 | Hughes et al. | 623/12 |
| 4,731,055 | 3/1988 | Melinyshyn et al. | 604/100 |
| 4,930,502 | 6/1990 | Chen | 606/150 |
| 5,078,735 | 1/1992 | Mobin-Uddin | 623/1 |
| 5,089,008 | 2/1992 | Chen | 606/216 |
| 5,211,683 | 5/1993 | Maginot | 623/1 |
| 5,399,352 | 3/1995 | Hanson | 623/1 |
| 5,443,497 | 8/1995 | Venbrux | 623/1 |
| 5,453,084 | 9/1995 | Moses | 623/12 |
| 5,456,712 | 10/1995 | Maginot | 623/1 |
| 5,480,424 | 1/1996 | Cox | 623/2 |
| 5,562,726 | 10/1996 | Chuter | 623/1 |
| 5,609,605 | 3/1997 | Marshall et al. | 623/1 |
| 5,643,340 | 7/1997 | Nunokawa | 623/1 |
| 5,653,743 | 8/1997 | Martin | 623/1 |
| 5,693,088 | 12/1997 | Lazarus | 623/1 |
| 5,755,778 | 5/1998 | Kleshinski | 623/1 |
| 5,800,522 | 9/1998 | Campbell et al. | 623/1 |

OTHER PUBLICATIONS

Literature: Don R. Wells, MS, Joseph P. Archie, Jr., PhD, MD, and Clement Kleinstreuer, PhD, "Effect of carotid geometry on the magnitude and distribution of wall shear stress gradients," Journal of Vascular Surgery vol. 23, No. 4, (1996) pp. 667–578.

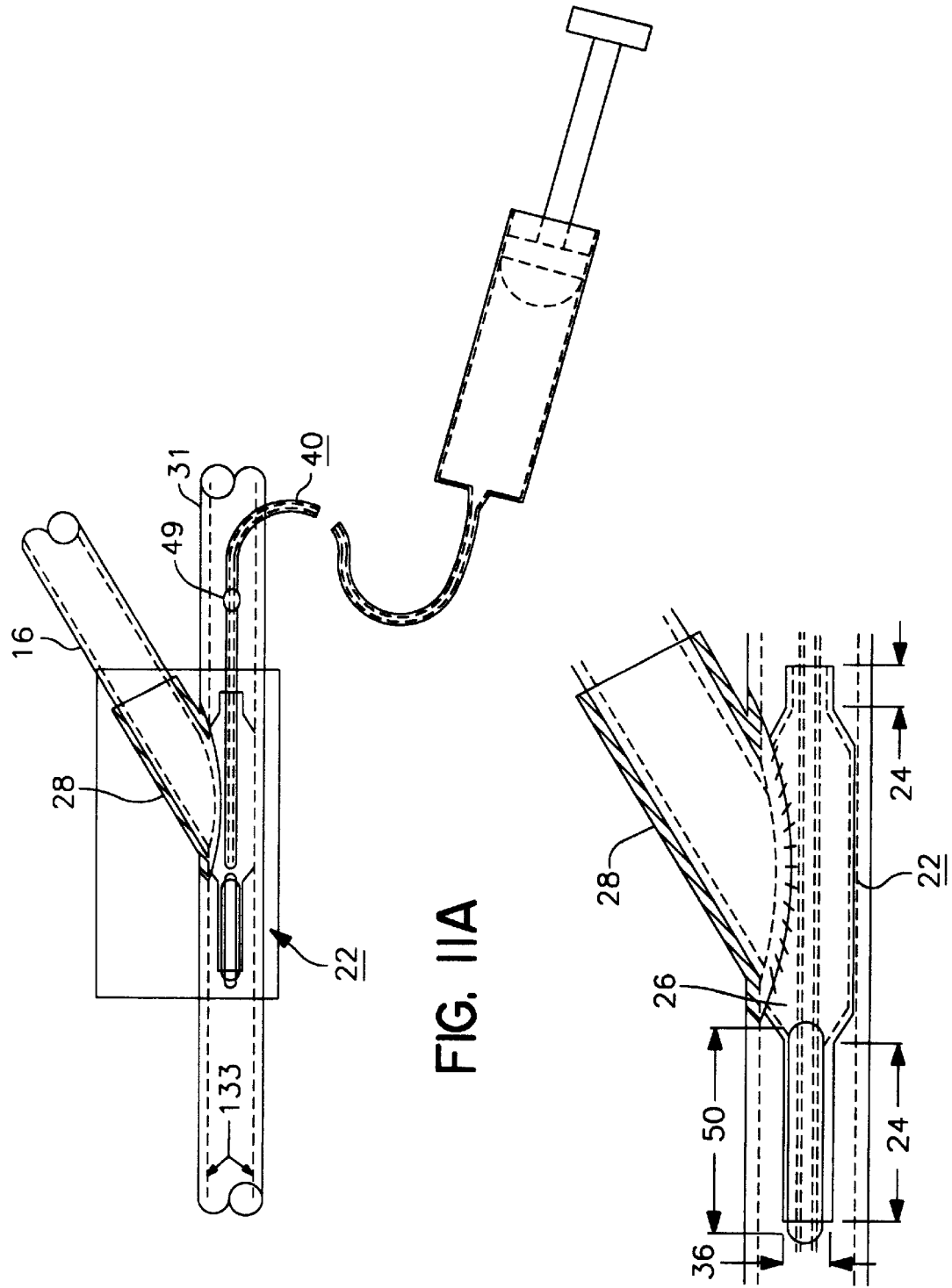
FIG. IIA
FIG. IIB

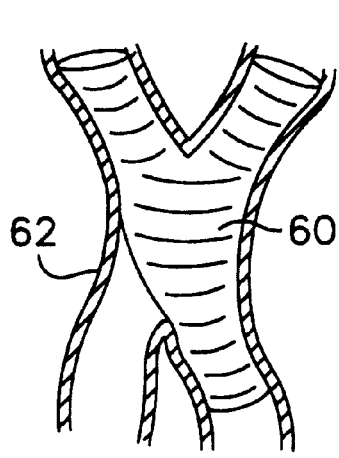
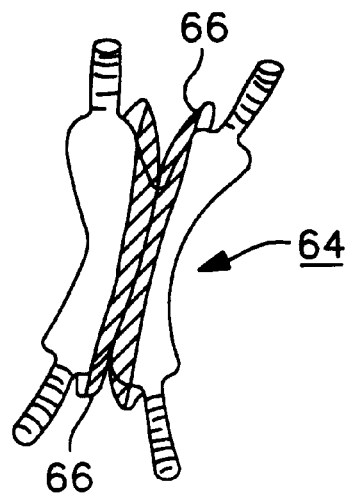
FIG. 15  FIG. 16
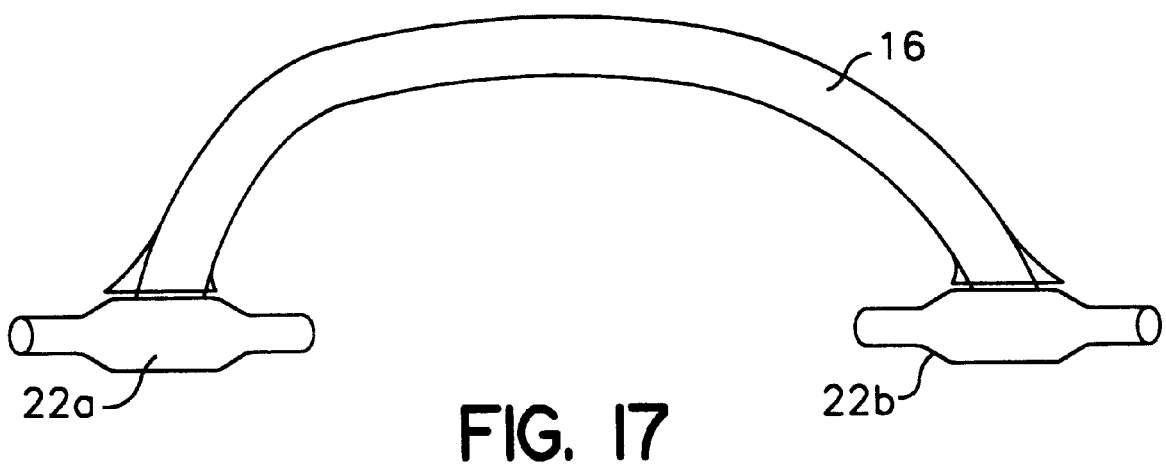
FIG. 17

VASCULAR SHUNT GRAFT AND JUNCTION FOR SAME

RELATED APPLICATIONS

The present application is a continuation-in-part of U.S. patent application Ser. No. 08/745,672, filed Nov. 8, 1996 now abandoned.

BACKGROUND OF THE INVENTION

1. Field of the Invention

The present invention relates to an implantable medical device, and more particularly, to an apparatus for connecting conduits in a body, such as forming an arterio-venous (AV) access fistula or arterial or venous bypass, and methods of constructing and deploying the same.

2. Description of Related Art

It is a common surgical procedure to implant a vascular graft between an artery and vein to create a shunt for dialysis access. Typically, these grafts comprise a biocompatible conduit, either autologous (vein or artery) or synthetic, which can withstand repeated cannulation during the course of prolonged therapy.

Among the preferred synthetic tubes for artery-vein (AV) access are any of a variety of expanded polytetrafluoroethylene (PTFE) vascular grafts sold by W. L. Gore & Associates, Inc., Flagstaff, Ariz., under the trademarks GORE-TEX® and DIASTAT®.

A similar surgical procedure is required when an artery or vein becomes occluded. A synthetic graft or autologous vein or artery is sutured to the vessel both upstream and downstream of the occlusion so as to conduct the flow of blood around the blockage. The most common synthetic grafts used in these applications are those made from polyethylene terephthalate material or expanded PTFE material.

Expanded PTFE vascular grafts exhibit numerous properties that make them particularly suited for the above applications, including being highly biocompatible, being relatively easy to handle and suture, and having suitable flow surface characteristics.

Despite the good performance characteristics of existing synthetic vascular grafts for AV access, the majority of the AV grafts fail in a relatively short period of time after implantation, thereby requiring surgical intervention. The primary cause of complications and failures with synthetic grafts used for AV access has been attributed, in large part, to venous anastomotic stenosis, or anastomotic hyperplasia. Anastomotic stenosis is a common failure mechanism of grafts used for arterial bypasses, as well.

Although the exact mechanism or mechanisms resulting in anastomotic stenosis are not fully understood, theories exist regarding its etiology. Stenotic anastomoses are thought to be a result of native vessel response to injury caused by surgical trauma, unnatural shear stresses, mismatch of mechanical properties between the graft and the native vessels, and/or disturbed hemodynamics. Additionally, disturbed flow may cause deposition of formed blood elements in the perianastomotic region, resulting in the release of growth factors that are chemotactic and/or mitogenic to fibroblasts and smooth muscle cells. The factors induce these cell types to migrate into the intima of the native vessel and proliferate, causing the anastomosis to become stenotic. The presence of suture or staple holes in the anastomotic region not only provide pathways through which cells can migrate, they are also areas of local injury which can lead to the release of growth factors. Through these mechanisms, suture or staples used in the construction of an anastomosis also increase the potential for anastomotic stenosis.

The present inventors believe that an improved implantable junction device designed to minimize the stenotic consequences of these effects should have the following features: 1) appropriate hemodynamics to minimize turbulence and inappropriate shear stresses on native arteries or veins; 2) implantation means that do not require sutures or staples that penetrate through to the luminal surface of the blood vessel or the device; 3) when used to join two streams of blood, isolation of the native vessel from direct impingement by the incoming stream of blood; 4) sufficient "impact isolation distance" from where the incoming stream of blood impinges to the end of the device; and 5) sufficient "cellular isolation distance" whereby cut and traumatized vessel tissues are isolated from the lumen so that cells are limited from migrating into and proliferating onto the luminal surface of the device or the native vessel. It is believed that an improved anastomotic junction incorporating the above features will address many of the issues related to anastomotic stenosis as a complication and failure mechanism of vascular grafts.

A number of devices have been proposed to provide a better junction in a blood vessel. For instance, T-shaped grafts that can be inserted into a severed end of a blood vessel have been proposed for various surgical procedures. U.S. Pat. No. 3,683,926 to Suzuki and U.S. Pat. No. 4,503,568 to Madras teach a number of different junctions for joining separated blood vessels, including T-shaped and Y-shaped junctions, generally referred to "Y-shaped" herein, that can attach together multiple blood vessels. While these devices may eliminate direct flow impact against the vessel wall at the junction, these devices have a number of other problems. First, surgeons generally attempt to preserve host vessels by avoiding unnecessary cutting and removal of sections of vessels. Both Suzuki and Madras teach complete severing of the blood vessel, which requires removal of a vessel segment to avoid redundancy. Second, excessive proliferation of normal cells has been observed at the interface between the severed blood vessel and the junction device. This excessive proliferation results in stenotic formations over a relatively short time frame. Another deficiency with the Suzuki device is that Suzuki's junction is readily soluble in blood. This is likely to lead to questionable anastomotic integrity and only temporary protection of the native vessel from the impingement of the incoming stream of blood. Given these deficiencies, it is not surprising that devices such as those taught by Suzuki and Madras are not widely used.

Some of these complications might be addressed if a junction device could be inserted into a blood vessel without requiring a complete severing of the blood vessel. Devices of this kind are disclosed in the U.S. Pat. No. 4,512,761 to Raible, U.S. Pat. No. 5,443,497 to Venbrux, and U.S. Pat. No. 5,456,712 to Maginot. A similar concept is disclosed in U.S. Pat. No. 4,230,119 to Blum, wherein Blum teaches a micro-hemostat that permits blood flow during vascular surgery. All of these devices are based on the concept of providing some junction device that is installed within the natural blood vessel. Unfortunately, such devices do not contain all of the features believed necessary to minimize anastomotic stenosis.

The Raible patent teaches a junction device for providing blood access external to the body. This device requires sutures at the device inlet, which, as has been noted, are believed to be undesirable. Similarly, the Maginot patent teaches using sutures or staples that pass from the outer surface to the luminal surface to attach the two components of his device. While Venbrux provides for sealing the penetration through the native vessel, he provides neither for an "impact isolation distance" nor for a "cellular isolation distance."

Accordingly, it is the primary purpose of the present invention to extend primary patency of an AV fistula or blood vessel bypass through the use of an improved junction device, where primary patency is defined as the length of time a graft remains patent without medical intervention.

It is a further purpose of the present invention to provide a medical junction device that can be relatively easily, uniformly, and consistently installed by a surgeon.

These and other purposes of the present invention will become evident from review of the following specification.

SUMMARY OF THE INVENTION

The present invention is an improved implantable medical junction device for providing a fluid connection between a blood conduit and a blood vessel. The design of the present invention incorporates a distensible intraluminal segment for placement inside the lumen of an artery or vein (the intraluminal segment), a sealed connection between the intraluminal segment and the blood conduit, and, preferably, a mechanism for anchoring the junction device to the native blood vessel.

The intraluminal segment is circumferentially distensible, having a first dimension proportioned to insert easily within the lumen of the blood vessel and a second circumferentially distended dimension proportioned to form a fluid tight seal by abutting the luminal surface of the blood vessel. The blood conduit is connected to the distensible intraluminal component at a hemodynamically appropriate angle that minimizes turbulent blood flow and inappropriate shear stresses. The attachment of the blood conduit to the distensible intraluminal component is performed using methods that do not puncture the blood conduit or the distensible intraluminal segment. Alternatively, other methods, such as suturing or stapling, can be used to construct the junction if the penetrations made by the sutures or staples are sealed. Optionally, an anchoring mechanism, or cuff, is provided as a means to attach the junction device to the blood vessel with sutures without creating penetrations to the blood contacting lumen of the blood vessel or junction device.

The distensible intraluminal segment is designed and positioned to create a "cellular isolation distance" and an "impact isolation distance." The cellular isolation distance separates the cut and traumatized edges of the venotomy or arteriotomy from the interior of the device, thereby preventing cells from migrating to and proliferating in the lumen. The impact isolation distance is the length of the distensible intraluminal component downstream of the area where the flow of blood from the blood conduit impacts the luminal surface of the distensible intraluminal segment. The impact isolation distance protects a length of blood vessel from direct intersecting blood impact by using the distensible intraluminal segment as a barrier. This distance allows the blood flow to become less turbulent and less prone to induce cell proliferation and migration before it contacts the blood vessel.

The distensible properties of the distensible intraluminal segment of the present invention enable the device diameter to be custom sized by the surgeon. For example, the surgeon may choose to create a fluid tight seal by distending the intraluminal segment of this invention to slightly larger than the initial blood vessel diameter. The surgeon may also choose to distend the intraluminal segment substantially larger than the initial blood vessel diameter for implantation into a vessel too small to implant by conventional surgical techniques. It also enables the device to be implanted with the optimal flow cross sectional area for intraluminal placement in vessels of varying diameters.

By manufacturing the distensible intraluminal segment of the present invention from materials that will retain their circumferentially distended dimension, this segment can be distended within the blood vessel and will retain a fluid-tight seal without the use of retention means, such as sutures or staples, that may puncture the blood vessel.

The term "circumference" is used herein to describe the external boundary of a transverse cross section of the article of the present invention. For any given amount of distention, the circumference is the same whether the article is wrinkled, folded, or smooth.

To further improve fluid tight sealing, anchoring, and attaching between the synthetic junction device and the host vessel, a cuff is taught that is attached to the blood conduit adjacent to the distensible segment. The cuff is proportioned to be attached to the venotomy or arteriotomy of the blood vessel after the distensible segment has been inserted intraluminally into the blood vessel. The cuff comprises a flap of material secured to and surrounding the blood conduit, whereby the cuff can be positioned by bending, rolling, or otherwise folding it away from the distensible segment prior to intraluminal insertion into the blood vessel. Subsequently, the cuff can be repositioned to the original position for attachment, such as by suturing or stapling, to the venotomy or arteriotomy. Alternatively, the cuff may comprise a ridge of material that encircles, either continuously or discontinuously, the junction between the distensible intraluminal segment and the blood conduit. Further, the microporosity, rigidity, morphology, and other physical properties of the cuff and distensible material may be varied to optimize the performance of this medical junction device.

In order to achieve inhibition of cellular proliferation and migration that might lead to stenosis or occlusion, it may be desirable for one embodiment of the present invention to provide the surface of the cuff that interfaces with the host vessel, with an expanded PTFE or other appropriate biocompatible material having a porous or microporous structure that allows and encourages in-growth and attachment of the host tissues. In another embodiment, the outer surface of the distensible segment may be constructed from a suitable microporous expanded PTFE or other appropriate biocompatible material that limits host tissue in-growth and attachment, preventing cellular proliferation and migration that might lead to stenosis or occlusion.

A preferred embodiment of the present invention comprises a blood conduit and junction formed from expanded PTFE or similar material or materials that can be easily implanted as an AV access graft for use in dialysis or as an arterial or venous bypass graft. The blood conduit of the present invention may also be provided in other forms such as tapered, stepped, reinforced, or leakage resistant vascular grafts. The junction device of the present invention may be used for various bypass applications whether or not endarterectomy procedures are required.

The device of the present invention can be easily implanted by a surgeon with minimal effort. Preferably, the distensible segment is quickly and effectively circumferentially distended in place using a balloon catheter, a mechanical distending tool, and/or by removing restraints that hold the device in the non-distended configuration.

Without intending to limit the present invention to such theories, the device of the present invention is believed to extend graft patency through one or more of the following mechanisms: (a) isolating injured and traumatized native tissues away from the luminal blood surfaces; (b) providing a hemodynamic interface with controlled design and configuration; (c) reducing turbulence at the anastomosis; and/ or (d) shielding the native blood vessel from the force of the impinging blood flow and unnatural shear stresses.

DESCRIPTION OF THE DRAWINGS

The function of the present invention should become apparent from the following description when considered in conjunction with the accompanying drawings, in which:

FIG. 11a illustrates a first step in a process of installing an embodiment of the device of the present invention within a blood vessel;

FIG. 11b is a detailed enlargement of the boxed portion of FIG. 11a;

FIG. 15 is a cross-section view of a deployed Y-shaped junction embodiment of the present invention mounted in a side-by-side vascular application that excludes a branch of the host blood vessel;

FIG. 16 is a side elevation view of a non-deployed X-shaped junction embodiment of the present invention, again adapted for mounting in a side-by-side vascular application;

FIG. 17 is a side elevation view of another embodiment of a device of the present invention, having junctions mounted on both ends of a blood conduit;

DETAILED DESCRIPTION OF THE INVENTION

The present invention relates to an implantable medical device for use in joining two blood conduits, such as required for arterio-venous (AV) access fistulas or bypassing an occluded blood vessel, as well as a method for manufacturing and deploying such a device. The device of the present invention resists stenotic formations within the conduit and at the interface of the device and the lumen of the blood vessel. While the present invention has a number of applications, for convenience, the present invention is described below with respect to creating an AV access fistula between an artery and vein. It should be understood, however, that the present invention is suitable for any application, including use in nonvascular tubular structures, that can be incorporated into the described configurations of the present invention.

Figure 1:
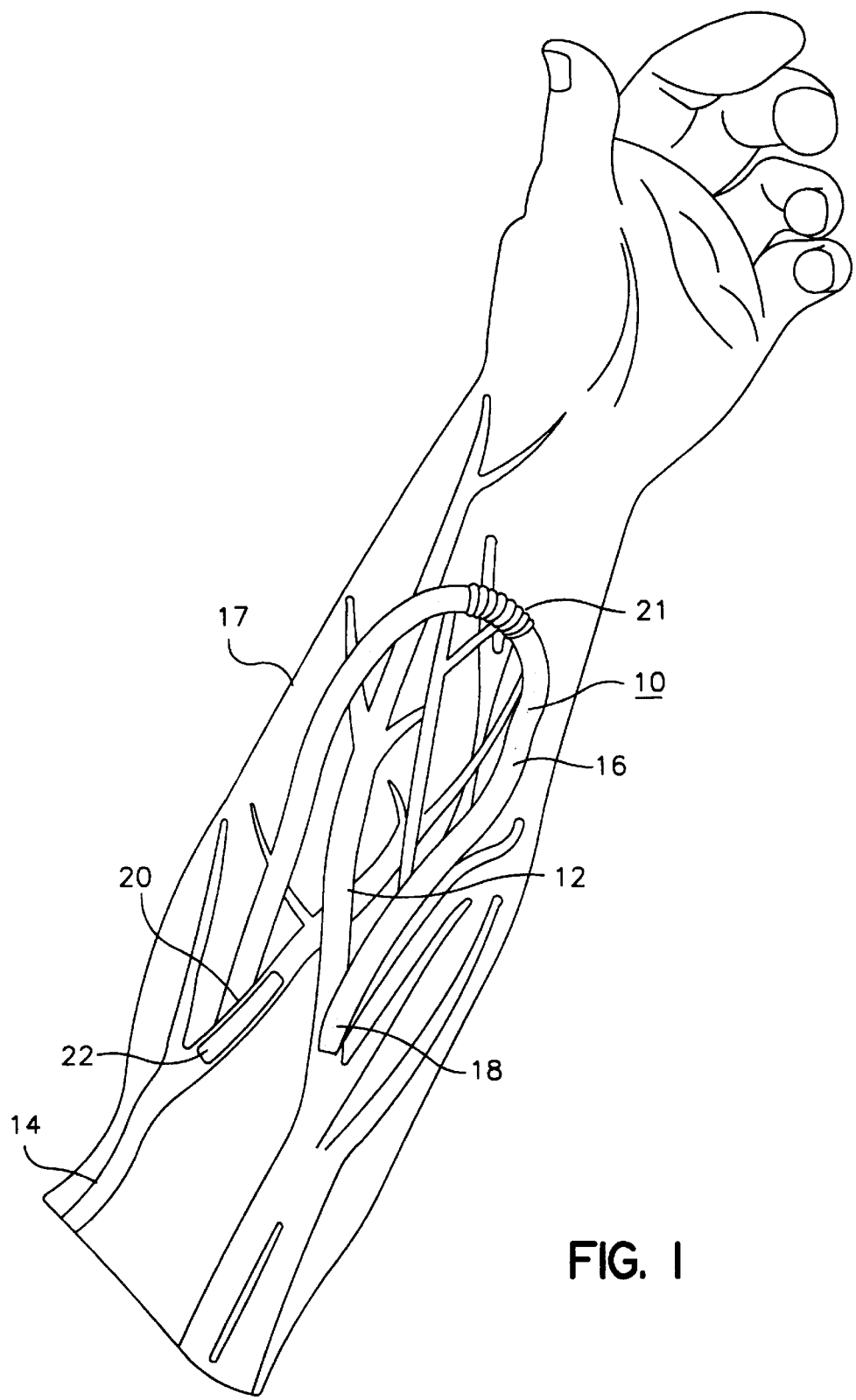
FIG. 1 is a top plan view of a patient's forearm showing a junction and blood conduit of the present invention in cut-away connecting between an artery and a vein.

FIG. 1 illustrates a device 10 of the present invention connected between an artery 12 and a vein 14 in a patient's arm 17. The device 10 comprises a blood conduit 16, and has a first end 18 attached to the artery 12 and a second end 20 attached to the vein 14. A distensible junction segment 22 of the present invention is inserted within the vein 14, as is explained in greater detail below. For clarity the junction segment 22 is shown unobstructed by the vein 14. In normal use the junction segment 22 is positioned intraluminally within the vein and would not be readily visible through the wall of the vein.

In this embodiment, the device 10 comprises a blood conduit, such as one used for hemodialysis treatments. The conduit 16 has a center portion 21 that is externally ringed to resist kinking in a full radius bend.

Figure 2:
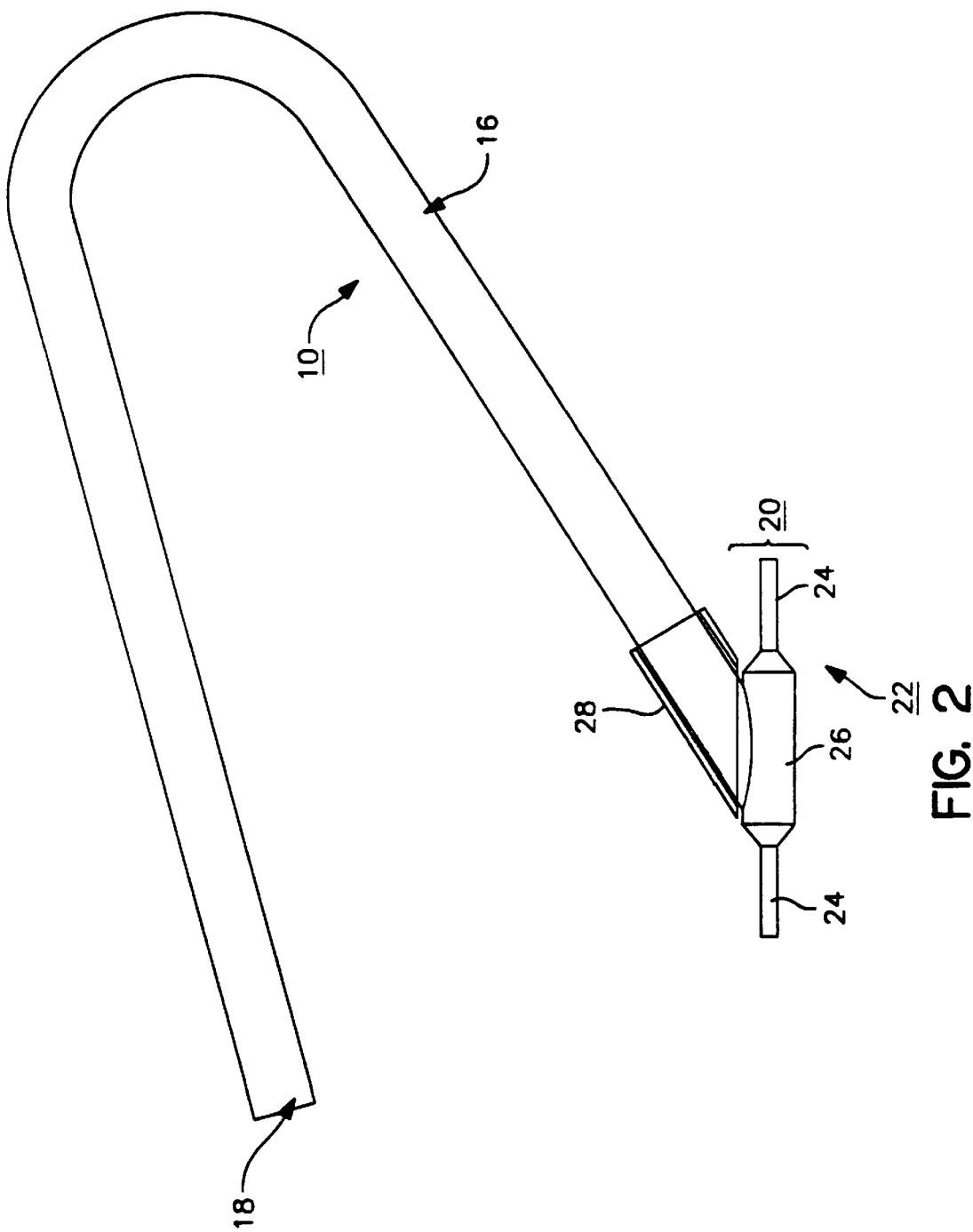
FIG. 2 is a side elevation view of the device of the present invention incorporating a junction of the present invention.

The device 10 of the present invention and the distensible junction segment 22 of the present invention are shown in greater detail in FIG. 2. The device comprises a distensible junction segment 22 of predetermined dimensions having contracted (i.e., non-circumferentially distended) segments 24 that are adjacent to a circumferentially distended midsection 26. The contracted segments 24 have a first dimension proportioned to insert easily within the blood vessel.

Firmly attached to the circumferentially distended midsection 26 of the distensible segment 22 is the conduit 16, preferably with an incorporated cuff 28. The cuff 28 may be provided on the conduit 16 to further improve the anchoring and fluid tight seal between the blood conduit and the attached blood vessel. The cuff 28 preferably comprises a flap of material that is attached to and surrounds the blood conduit adjacent to the circumferentially distended midsection 26. The cuff 28 is proportioned to be attached to the venotomy of the blood vessel once the distensible junction segment 22 has been completely inserted therein, to form a further improved seal between the device 10 and the blood vessel and to provide additional anchoring to the blood vessel. The cuff 28 assures that, in the event that any blood seeps around the outer periphery of the deployed distensible segment 22 of the present invention, an additional means is provided to prevent leakage from the blood vessel.

The cuff may be attached to the venotomy of the blood vessel 14, such as the venotomy shown in FIG. 1, through any suitable means, although sutures, surgical staples, and/or bio-adhesives are particularly preferred.

The device of the present invention is preferably made from porous polytetrafluoroethylene (PTFE) and most preferably a porous expanded PTFE having a microstructure of nodes interconnected by fibrils, such as that taught by U.S. Pat. Nos. 3,953,566 and 4,187,390 to Gore, both of which are herein incorporated by reference. The pore size of the porous PTFE is preferably such that the device is substantially impervious to leakage of blood and consequently does not require pre-clotting. Further, the microporosity and other physical properties of materials comprising the components of this invention may be varied to optimize performance for particular applications.

The attachment of the blood conduit to the distensible junction segment of the present invention should be constructed in a manner that limits cellular migration through the seam line and attachment holes between the conduit and the junction. Suitable attachment methods may include sutures, staples, bio-adhesives, or other means of bonding the two elements together. If attachment methods, such as sutures or staples, are used in a manner that creates passages from the abluminal surface of the device through to the luminal surface, the holes should be sealed to prevent cellular migration through the holes. The blood conduit may be provided in straight, tapered, stepped, or other forms. The conduit may also be formed from existing commercially available grafts, such as GORE-TEX® vascular grafts or DIASTAT® vascular grafts, both available from W. L. Gore & Associates, Inc., Flagstaff, Ariz.

Further, the microporosity and other morphologies of the materials comprising the device may be varied to optimize performance. For example, in one embodiment, it may be desirable to provide a device with a cuff having open microporosity to encourage localized cellular in-growth, attachment, and inhibition of migration of specific cells and tissues from entering the lumen of the host vessel. In another embodiment, it may be desirable to provide a device with a cuff having a closed microporosity to discourage localized cellular in-growth and attachment.

It should be appreciated that the implantable medical device of the present invention may comprise a single material or, alternately, may be a multi-compositional device. Suitable materials include any biocompatible materials and may be of any desirable microporosity, morphology, rigidity, etc. For example, suitable materials may include PTFE, expanded PTFE, silicones, urethanes, bio-absorbable or resorbable polymers, other biocompatible materials, modified hyaluronic acid, and hydrogels.

It is preferred that the cuff 28 be constructed from the same material as the blood conduit 16, with the preferred cuff manufactured of expanded PTFE with expanded PTFE film wrapped and heat sealed to the blood conduit. Additional means of attachment of the cuff to the blood conduit include, but are not limited to, sutures and adhesives. Further, the microporosity and other morphologies of the materials comprising the cuff may be varied to optimize performance.

Figure 3:
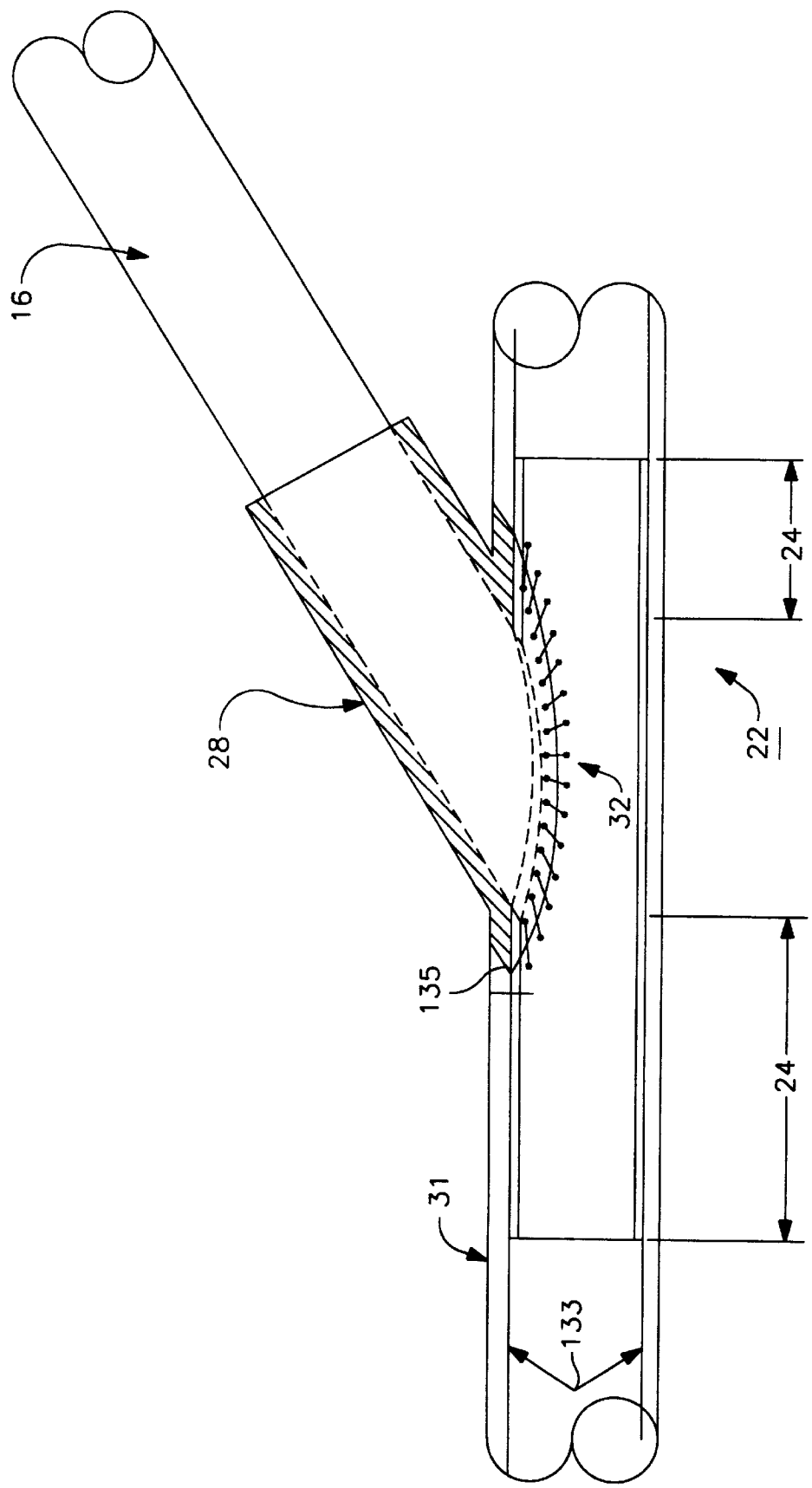
FIG. 3 is a side elevation view of a device of the present invention shown in phantom fully distended within a blood vessel and with a cuff of the present invention shown sutured to a venotomy/arteriotomy of the blood vessel.

FIG. 3 illustrates how the junction 22 of the present invention is oriented in a blood vessel 31 once fully deployed. As is shown, distensible segments 24 are distended within the blood vessel 31 to form a fluid-tight seal with the blood vessel's luminal surface 133. Additionally, FIG. 3 illustrates in detail a method of connecting, anchoring, and sealing the junction 22 and cuff 28 to an incision 135 in the blood vessel 31. In the embodiment illustrated, the cuff 28 is attached to the blood vessel 31 using sutures 32.

By forming the distensible segment 24 from a material that will retain its enlarged dimension, the complete distensible segment 22 can be enlarged within the blood vessel and will retain a fluid-tight seal within the blood vessel 31 without the use of retention means, such as sutures or staples. It is believed that in this manner, the distended junction segment 24 will provide an adequate seal of the luminal surface and cellular isolation that will discourage excessive cell proliferation and migration along luminal surface 133 of the blood vessel 31 or into the distensible segment 22. As a result, the distended distensible junction segment 22 of the present invention is believed to be far less prone to stenotic formations than previous vessel junction devices or standard end-to-side anastomoses.

While use of a cuff 28 is preferred, it should be appreciated that the incision 135 in the blood vessel 31 may be sealed through a variety of means without departing from the present invention. For example, the incision can be sewn or stapled or glued closed around the blood conduit 16. Additionally, the incision may be closed around the blood conduit and then additionally sealed using the cuff.

Figure 4:
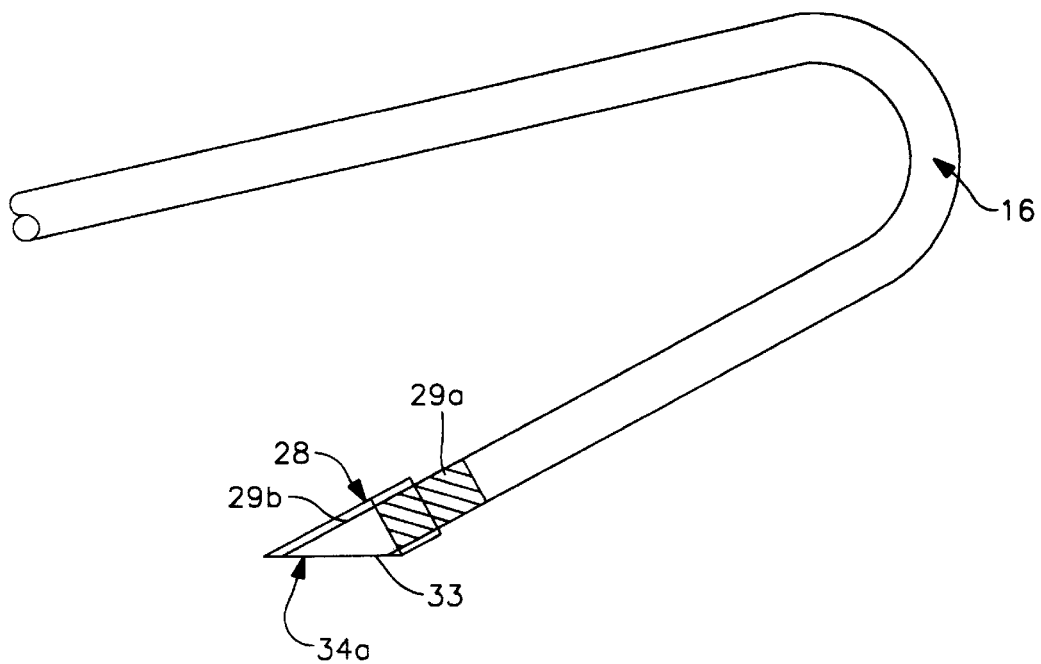
FIG. 4 is a side elevation view of a blood conduit and cuff of the present invention, with the cuff shown in an extended position.

As shown in FIG. 4, it is preferred that the cuff 28 of the present invention is firmly attached to the blood conduit at position 29a and is not attached to the blood conduit at position 29b so that the cuff 28 can be folded (i.e., bent, rolled, or otherwise folded) away from the distensible junction segment (not shown) during initial insertion and then folded toward the distensible junction segment 22 for attachment to the blood vessel. As is seen in FIGS. 4 through 6, the ability to fold or roll the cuff 28 also assists in the attachment of the distensible junction segment 22 to the blood conduit 16 during device fabrication.

FIG. 4 shows the blood conduit 16 and the cuff 28 of the present invention with the cuff shown in the extended position. FIG. 5 shows the blood conduit 16 and cuff 28 of the present invention with the cuff 28 shown in the folded position. FIG. 6 shows the blood conduit 16 and cuff 28 with the cuff shown in the folded position so that the blood conduit 16 can be readily attached to the distended midsection 26 of the distensible junction segment 22 during device fabrication. In the embodiment shown, the blood conduit 16 and the distended midsection 26 are being attached together by suture 27 that will form a sewn seam once the suture is drawn tight and knotted. It should be understood that the use of the term "suture" herein is intended to refer to any thread-like material that can be used to sew a seam.

It is preferred that pre-formed holes 33 be provided in both the blood conduit 16 and in the junction segment 22 to allow for ready lacing of sutures or other attachment means. The pre-formed holes 33 should be aligned to provide the correct orientation between the two components. The pre-formed holes 33 may be created through any suitable means, including laser cutting or punching-out with a cutting or piercing device.

Figure 5:
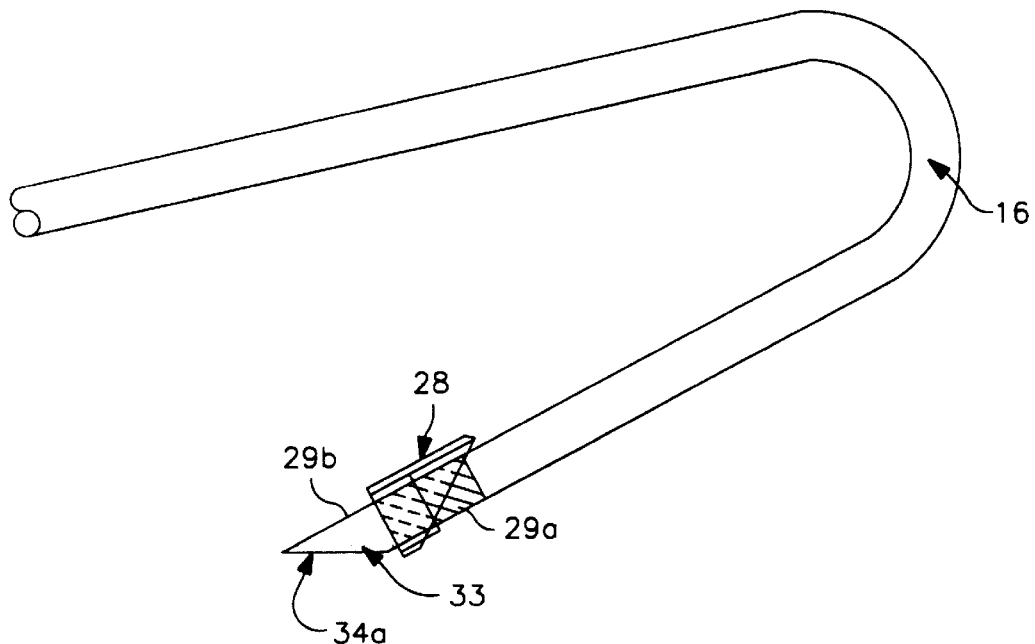
FIG. 5 is a side elevation view of a blood conduit and cuff of the present invention, with the cuff shown in a folded position.
Figure 6:
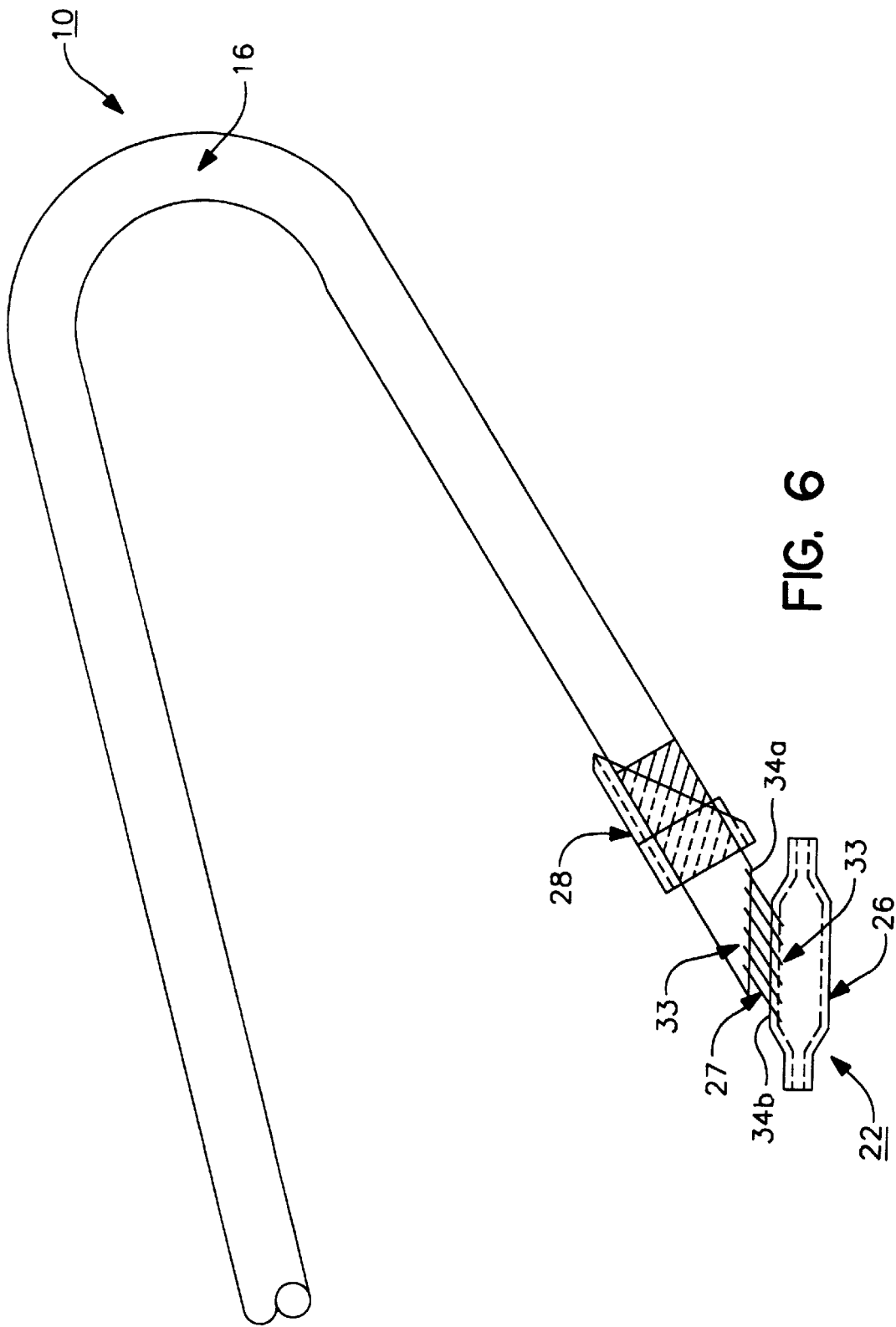
FIG. 6 is a side elevation view of a blood conduit and cuff of the present invention, with the cuff in a folded/rolled position with the blood conduit oriented for suture attachment to a circumferentially distended midsection of the distensible segment of the present invention.

In the embodiment shown in FIGS. 4 through 6, the distended midsection 26 of the distensible junction segment 22 and the blood conduit 16 are each provided with an opening 34a and 34b, respectively, that allow the two components to be attached together using the suture 27 to form a continuous open conduit.

Figure 7A:
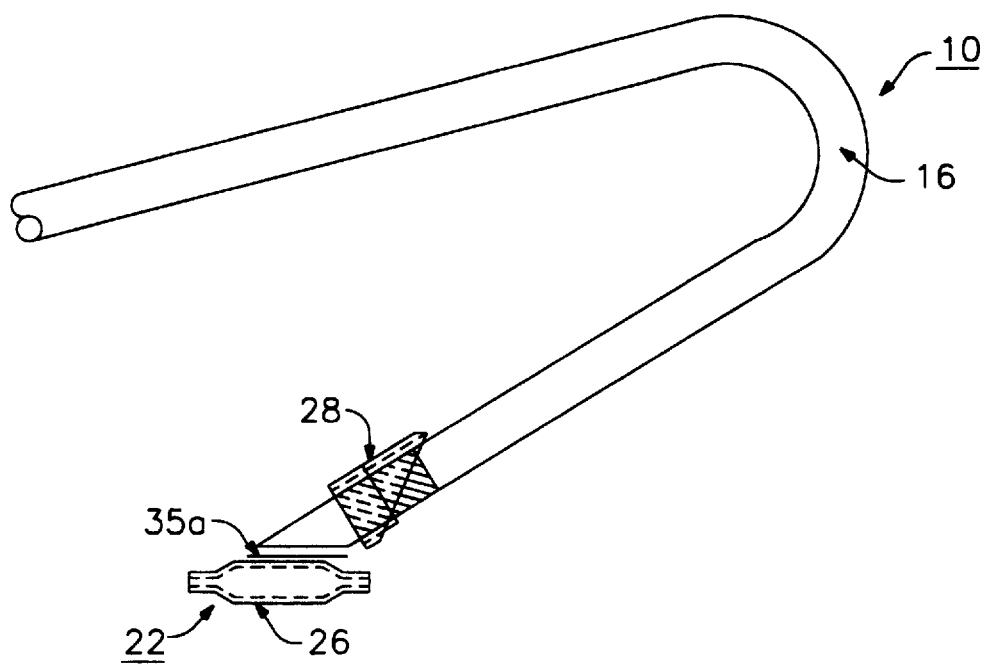
FIGS. 7a through 7d illustrate an additional embodiment of an attachment means for joining a blood conduit to the distensible junction segment of the present invention.
Figure 7B:
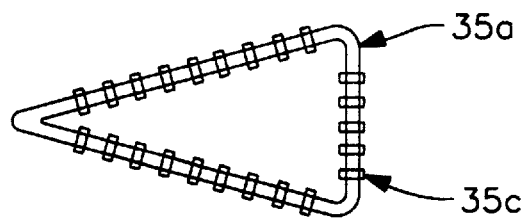
Figure 7C:
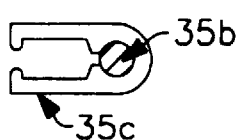
Figure 7D:
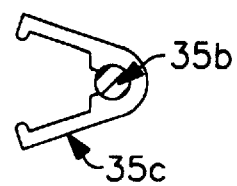

In the embodiment shown in FIGS. 7a through 7d, the blood conduit 16 and the distended mid-segment 26 are being attached together by an anastomotic connector 35a which comprises a pre-formed anastomotic member 35b with incorporated staples 35c to form a fluid tight seam line once the staples are crimped, as seen in FIG. 7c. The pre-formed anastomotic member 35a may comprise any biocompatible material and may be of any desirable microporosity, morphology, rigidity, etc. For example, suitable materials may include PTFE, expanded PTFE, fluorinated ethylene propylene (FEP), perfluoroalkoxy polymer (PFA), silicones, urethanes, bio-absorbable or resorbable polymers, other biocompatible materials, modified hyaluronic acids, hydrogels, perfluoroelastomers, and stainless steel. FIG. 7d shows an incorporated staple 35c in a pre-crimped position in which the preformed anastomotic member 35b is captured within the incorporated staple 35c.

One preferred method of manufacturing the cuff assembly 28 and attaching the cuff 28 to the blood conduit 16 of the present invention is described below and illustrated in FIG. 8a through 8e.

Figure 8A:
FIGS. 8a through 8e illustrate one embodiment of a process of producing a cuff assembly of the present invention and anchoring the cuff to the blood conduit of the present invention.
Figure 8B:
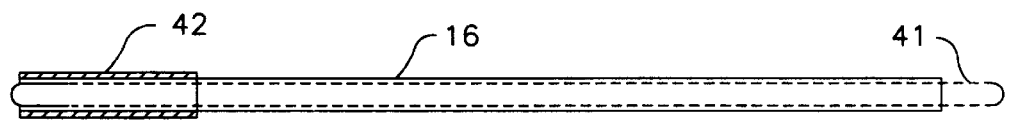
Figure 8C:
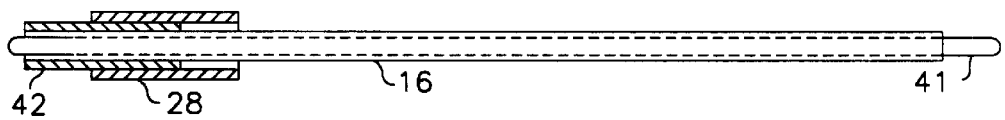
Figure 8D:
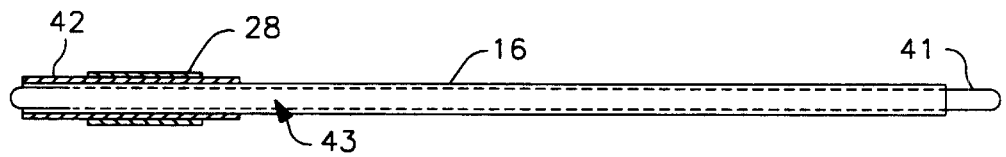

FIG. 8a illustrates a mandrel 41, such as one constructed from stainless steel, inserted inside a blood conduit 16. FIG. 8b illustrates a stainless steel cuff sleeve 42 located over a single end of a blood conduit 16. FIG. 8c illustrates the cuff 28 being placed over the stainless steel cuff sleeve 42 such that it extends beyond the end of the sleeve 42 onto the blood conduit 16. FIG. 8d illustrates an expanded PTFE film 43 wrapped over the cuff 28 and blood conduit 16 in which a portion of the cuff 28 is isolated from the blood conduit 16 by the stainless steel cuff sleeve 42. The composite device thus formed and illustrated in FIG. 8d is then placed in a convection oven set at a temperature of about 370° C. for about 10 minutes. Upon removal from the oven, the assembly is air cooled, then the stainless steel mandrel 41 and stainless steel cuff sleeve 42 are removed from the cuff assembly 28 and blood conduit 16.

Figure 8E:
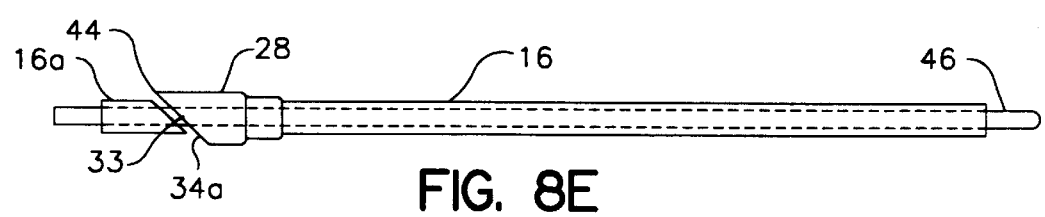

FIG. 8e illustrates a laser mandrel 46, again constructed from a material such as stainless steel, inserted inside the cuff 28 and blood conduit 16 assembly. Subsequently, opening 44 is provided between the cuff 28 and blood conduit 16 to allow the cuff to be folded back for access of the blood conduit 16 to be attached to the distended mid-segment 26 of the distensible junction segment 22 during device fabrication. Any excess blood conduit 16a is removed from the laser mandrel 46 and discarded. The location and geometries of the laser cuts may be any necessary to achieve the desired orientation to optimize attachment and flow surface matching between the blood conduit 16 and the distensible junction segment 22.

The angle of attachment between the blood conduit and the junction may be varied from anywhere essentially between 0 to 180 degrees (in reference to the blood conduit and distensible segment). For example, the geometry of the device may be tailored for anatomical differences between patients and procedures (for instance, for attachment to either shallow or deep vessels) by varying physical geometries, angles, radii, dimensions, rigidities, physical forms, and the like.

For most applications, the angle of attachment between the conduit and junction will be about 10 to 90 degrees off the longitudinal axis of the distensible junction segment, with about 15 to 45 degrees preferred. It is most preferred to have an angle of attachment between the conduit and the junction at about 25 to 35 degrees (that is, around 30 degrees) off the longitudinal axis of the distensible junction segment.

It is preferred to form the opening 34a and angled geometries using a laser, such as a 20 watt $CO_2$ laser (e.g., a Model 2010 $CO_2$ laser available from Universal Laser, Inc., of Scottsdale, Ariz., having a 6.35 mm focal length lens). Opening 34a and suture holes 33, shown in FIG. 5, should also be provided through the blood conduit 16 at appropriate location, spacing, and distance to provide a uniform and consistent means of attachment of the blood conduit 16 to the distended mid-segment 26 of the distensible junction segment 22, as shown in FIG. 6.

The construction of the distensible junction segment 22 is believed to be of particular note in the present invention. As has been explained, previous Y shaped junctions have not been effective at avoiding stenotic formations. One problem in this respect is believed to be the fact that many of these previous junctions had to be sewn through the vessel wall, providing a site for excessive cell proliferation, blood flow turbulence, etc. The present invention avoids this problem by providing a distensible junction segment 22 that can be expanded in place to form a fluid tight seal against the luminal surface of the blood vessel 133. This tight seal allows the distensible junction segment 22 to remain in place without the need to suture its ends to the blood vessel and with minimal risk of blood leaking around the periphery of the distensible junction segment 22. Additionally, the present invention provides a hemodynamic interface between the blood conduit 16 and the distensible junction segment 22 on an optimized angle.

The distensible junction segment 22 assembly of the present invention is preferably constructed as follows. A longitudinally extruded and expanded porous PTFE tube is obtained and fitted coaxially over a stainless steel mandrel having an outside diameter the same as or slightly larger than the inside diameter of the porous PTFE tube. The ends of the tube are then pushed together so that the length of the tube is reduced at least about 50%, and preferably about 20%, of the original length of the tube prior to this longitudinal compression. The tube and mandrel are then heated in an air convection oven set at about 380° C. for approximately 50 seconds. Next, predetermined regions of the compressed tube are heat treated with a laser. Subsequent to the laser treatment and cooling, the tube is removed from the mandrel. With moderate tension applied to the ends of the tube, the portions not treated by the laser extend out to their original length. The portions treated by the laser, however, are not readily extendible. These denser portions provide the radial support to the tube. The above process is described in steps 1 through 6 in the process flow chart depicted in FIG. 9.

Further processing the tube and creating a film tube as outlined in steps 7 through 13 of the flow chart provides a distensible, radially supported tube that can be subjected to internal pressure to circumferentially distend the tube up to a second circumference. With increasing pressure, the circumference changes very little beyond this second circumference; ultimately, the tube will burst without having dilated much beyond the second circumference. Film tube bonding, as described in step 9, and film tube bonding to the PTFE tube in step 12 are performed at about 380° C. The film may be made following the teachings of U.S. Pat. Nos. 3,953,566 and 4,187,390 to Gore.

Tube material for use in the present invention preferably is made to have a second circumference beyond which the circumference of the tube will not distend significantly unless the normal system operating pressure is substantially exceeded. For example, for intraluminal implantation, it is believed to be desirable for the tube to withstand pressures in excess of 25 times normal human systolic blood pressure (120 mm Hg) before the tube substantially increases in circumference beyond its second circumference. One embodiment of a tube would, for example, have an initial inside diameter of about 3 mm prior to circumferential distension. This small initial diameter allows for easy insertion into blood vessels. The second circumference of this embodiment would correspond to an inner diameter of, for example, 7 mm, so that the tube would be most useful for being inserted into blood vessels having inside diameters of up to about 7 mm. The second circumference is established by the presence of the thin film tube of helically wrapped porous PTFE film. The film tube can be bonded to the outer surface of a substrate tube of porous PTFE. This PTFE tube material is preferably made by longitudinal extrusion and expansion to create a seamless tube.

Alternatively, it is believed that the tube may be made from a layer of porous PTFE film oriented substantially parallel to the longitudinal axis of a tube and having a seam in this same direction. The helically wrapped porous PTFE film comprises primarily fibrils oriented in the substantially circumferential direction around the outer surface of the substrate tube, thereby restraining and limiting the second circumference of the resulting tube. The helically wrapped porous PTFE film is preferably wrapped in multiple passes applied in opposing directions with respect to the longitudinal axis of the tube. It is believed that such a tube may also be made from a porous PTFE film wrapped helically in opposing directions without the use of a separate substrate tube. Conversely, the tube material may be made so as to not have a second circumference for applications not requiring additional circumferential strength; in this manner, there is no pre-established limit to the circumferential growth of the graft.

Figure 9:
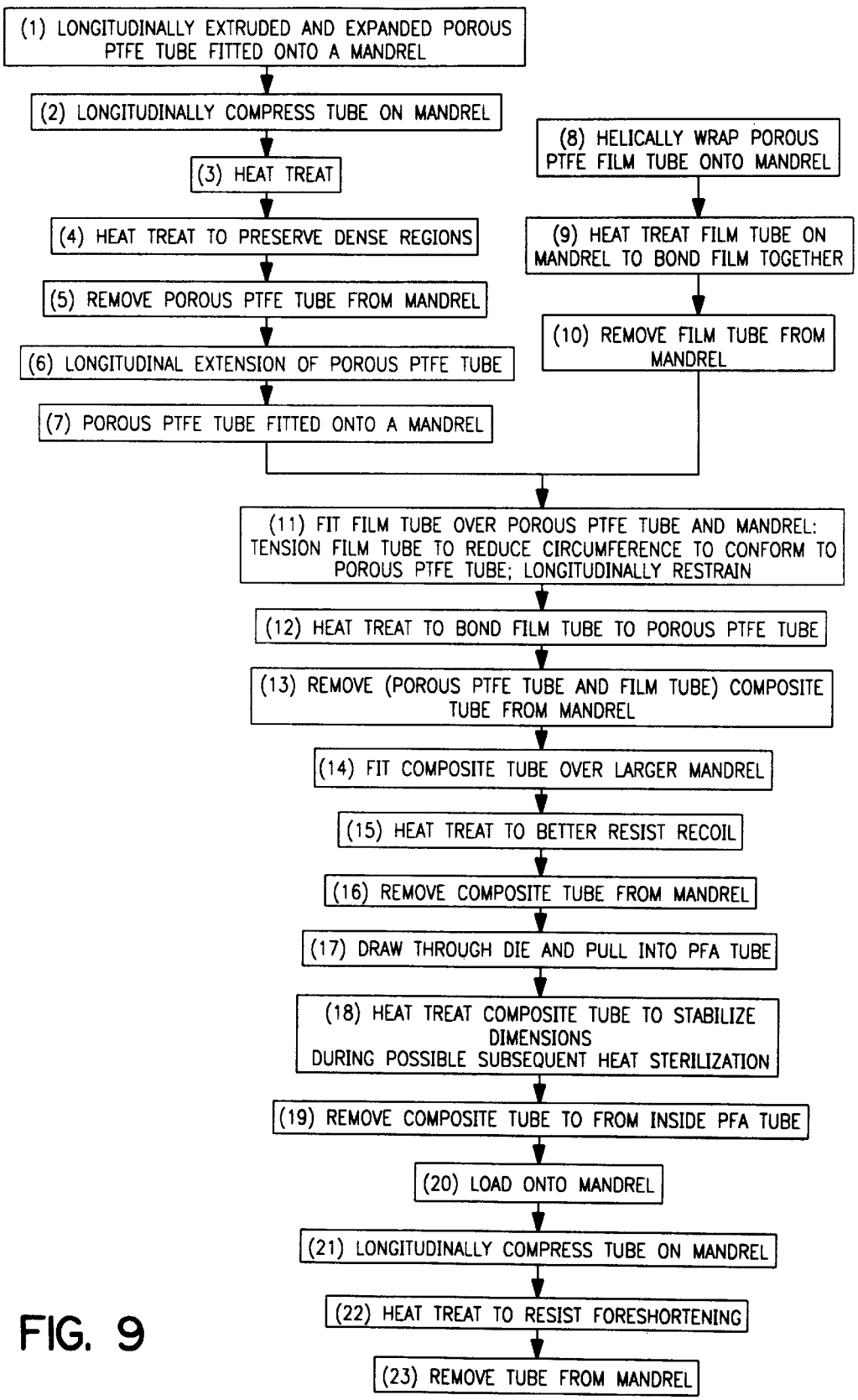
FIG. 9 is a process flow chart showing a method of creating a tube material for the distensible segment of the junction of the present invention.

The distensible, radially supported tube as produced by the following steps 1 through 13 of FIG. 9 can be further treated to provide resistance to recoil by completing steps 14 and 15. The heat treatment of step 15 serves to minimize tube recoil subsequent to circumferential distension. The heat treatment of step 18 serves to minimize dimensional changes associated with potential subsequent steam sterilization processes. These two heat treatment steps are performed at about 380° C. and about 200° C., respectively. Steps 20 through 22 minimize the foreshortening of the tube during subsequent circumferential distension.

The percentage recoil of the tube is determined with the use of a tapered metal mandrel having a smooth, polished exterior surface. A suitable taper is about 1.5° from the longitudinal axis. Preferably the mandrel is provided with incremental diameter graduations at intervals whereby the inside diameter of a tube may be determined by gently sliding a tube onto the smaller diameter end of the mandrel and allowing the tube to come to rest against the tapered mandrel surface and reading the appropriate graduation. Alternatively, the inside diameter of the tube may be measured by viewing the tube and mandrel, fitted together as previously described, using a profile projector measurement system. Using either a graduated mandrel or a profile projector, percentage recoil of a tube is determined by first measuring the initial diameter of the tube. The tube is then gently slid further onto the tapered mandrel with a minimum of force until a diameter increase of 25% is obtained. This increased diameter is considered to be the distended diameter. The tube is then pushed from the mandrel avoiding the application of tension to the tube. After waiting at least 30 minutes to allow the tube to recoil, the recoil diameter is determined using the tapered mandrel by performing the same procedure as used to measure the initial diameter. Percentage recoil is then determined using the formula:

$$\frac{\text{Distended diameter} - \text{recoil diameter}}{\text{Distended diameter}} \times 100 = \% \ recoil.$$

"Resistance to recoil" as used herein is considered to mean articles exhibiting a percentage recoil value of 14% or less and more preferably 10% or less.

The laser treatment described in step 4 of FIG. 9 can be performed in a number of ways. The following parameters can be varied to provide tubes with varying degrees of kink and compression resistance. Ring, helical spiral, and Z-shaped patterns that extend completely around the tube, and combinations thereof, can be applied to the tube via the use of the laser. In the embodiment illustrated in the drawings, ring-shaped regions are created. Upon subsequent extension, the tube retains denser areas exhibiting the patterns. The patterns can also be applied by a variety of heat treatment processes, such as by wrapping wires around the exterior of the tubes followed by heating the wire. The temperature chosen, the duration of the application of temperature, and the duty cycle of the application of thermal energy may each be changed to establish varying degrees of thermal treatment. The process also can be modified to provide different heat treatment through the wall thickness of the tube. The compression resistance of the dense area can be modified by varying the degree of longitudinal compression in step 2 and by varying the width and spacing of the pattern. The dense regions can be subjected to less thermal treatment so that the compressed material can be extended upon the application of moderate axial tension.

The process for creating a distensible junction segment for use in the present invention is described in detail in U.S. patent application Ser. No. 08/592,912, filed Jan. 29, 1996, now allowed, published as PCT Application PCT/US96/19301 on Aug. 7, 1997, each incorporated by reference.

It should be appreciated that other means of creating a distensible junction segment may be employed without departing from the present invention. For example, the junction segment may comprise a tube having an expandable stent element associated therewith. Like the device described above, the stent element will retain its enlarged size within a blood vessel without need for sutures or staples to hold it in place. Suitable stents may include metals, plastics, ceramics, or other materials, or combinations thereof.

Whether the junction segment comprises a material having specially treated segments that retain enlarged dimensions, such as that described above as the preferred embodiment, or comprises a multiple component structure, such as a tube and stent combination, or some other construction, this property of retaining enlarged dimensions once the junction segment has been installed and expanded within a blood vessel is generally referred to in this application as providing a "structure that assists in retaining an enlarged dimension."

Figure 10A:
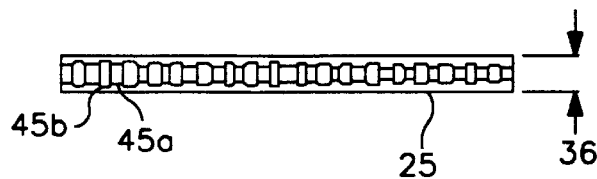
FIGS. 10a through 10d illustrate one embodiment of a process of circumferentially distending the mid-segment and locating the incision and suture holes of the distensible junction segment of the present invention.
Figure 10B:
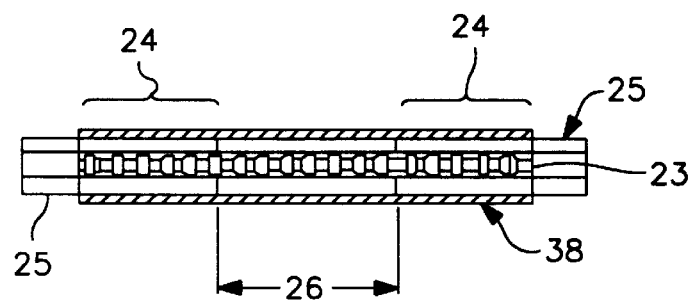

The method of manufacturing the distended midsection 26 of the distensible junction segment 22 is described below and illustrated in FIGS. 10a through 10d. FIG. 10a illustrates distensible material 23 used for the distensible junction segment 22 as described above. As previously described, the material includes alternating first and second ring regions 45a, 45b comprising the densified (heat treated) and non-densified (non-heat treated) material. As illustrated in FIG. 10b, the distensible material 23 is inserted inside two stainless steel end sleeves 25 located on its two ends. The internal diameter of each of the stainless steel end sleeves 25 is approximately equivalent to the outer diameter 36 of the distensible material 23. The stainless steel end sleeves 25 are located so as to cover the ends of the distensible material 23 and extend beyond the distensible material's ends, as is shown in FIG. 10b. During this process, the covered ends will be restrained from distending. The distance between the stainless steel end sleeves 25 determines the length of the circumferentially distended midsection 26 of the distensible junction segment 22.

As illustrated in FIG. 10b, a stainless steel center sleeve 38 is positioned over the non-distended midsection 26 of the distensible junction segment 22 to limit the circumferentially distended outer diameter. The internal diameter of the stainless steel center sleeve 38 should be greater than or approximately equal to the maximum inner diameter of the blood vessel that will ultimately receive the junction. A device of the present invention can be used in a range of diameters, from non-distended to fully distended. The length of the stainless steel center sleeve 38 should exceed the maximum length of the circumferentially distended mid-segment 26 of the distensible junction segment 22.

Figure 10C:
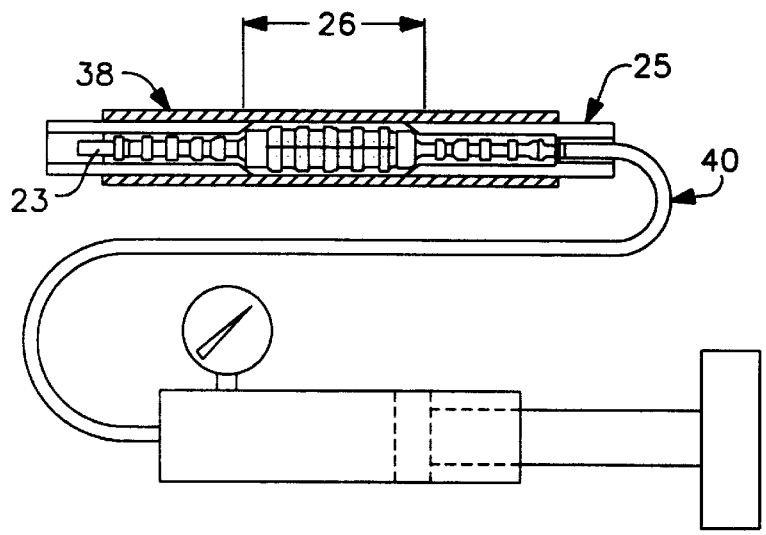
Figure 10D:
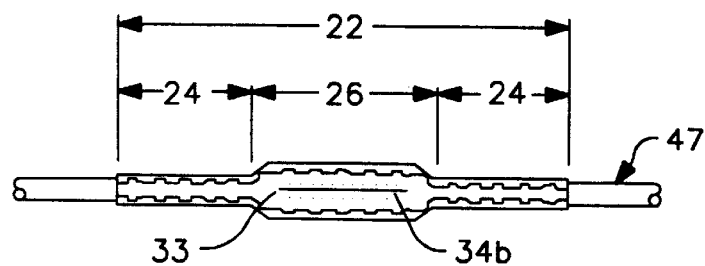

As is shown in FIG. 10c, an expansion device, such as a balloon catheter assembly 40, is inserted into the material 23. The expansion device is positioned longitudinally within the material 23 to accurately correspond to the desired location to create the distended mid-segment 26. The expandable portion of the expansion device 40 should exceed the desired length of the distensible mid-segment but remain within the outer boundaries of both stainless steel end sleeves 25. The stainless steel center sleeve 38 is positioned over the mid-segment 26. The expansion device 40 is then pressurized and deflated repeatedly. For example, the device may be pressurized to approximately 12 ATM for 60 seconds, then deflated for 60 seconds, then re-inflated to approximately 12 ATM for 60 seconds, then deflated and removed. Upon removal of the stainless steel end sleeves 25 and the stainless steel center sleeve 38, the distensible junction segment 22 is removed and is ready to be prepared for attachment to the blood conduit.

As has been explained, one method of attachment of the junction to the blood conduit is to pre-form suture holes and access incision in the distended mid-segment 26. The preferred method of forming such holes and incision is by employing a laser, such as through the method illustrated in FIG. 10d. As is shown, a stainless steel laser mandrel 47 is inserted inside the distensible junction segment 22. Subsequently, the circumferentially distended mid-segment 26 of the distensible junction segment 22 is laser cut to form the access incision 34b to the desired length and geometry using a laser or other cutting device, such as the $CO_2$ laser described previously. Additionally, laser holes 33 may be created through the circumferentially distended mid-segment 26 at optimal locations, spaced from the edge to provide a means of attachment to the blood conduit 16 assembly.

As has been previously shown and described with relation to FIG. 6, once suitable holes have been formed, the distensible junction segment 22 and the blood conduit 16 can be attached together, such as by lacing with suture material 27 through the laser holes 33 of the blood conduit 16 and through the laser holes 33 of the distended mid-segment 26.

After the lacing procedure using suture material 27 has been accomplished, the sutures may be individually tensioned to create a balanced and uniform seam line. Upon completion of such tensioning and knotting, the seam line and suture holes 33 may be sealed to further prevent blood leakage therethrough, such as through use of a silicone sealant (e.g., Silicone-Med 1137 commercially available from NuSil Silicon Technology, Carpinteria, Calif.). It may be desirable to thin the silicone sealant prior to application, such as through use of N-heptane-J338-3, commercially available from VWR/Baxter Healthcare, Irvine, Calif. This sealing procedure is also believed to be beneficial in reducing or eliminating cellular migration through the seam line and suture holes 33. It should be appreciated that other biocompatible materials may be used to seal the seam line and suture holes 33 without departing from the present invention.

Figure 11C:
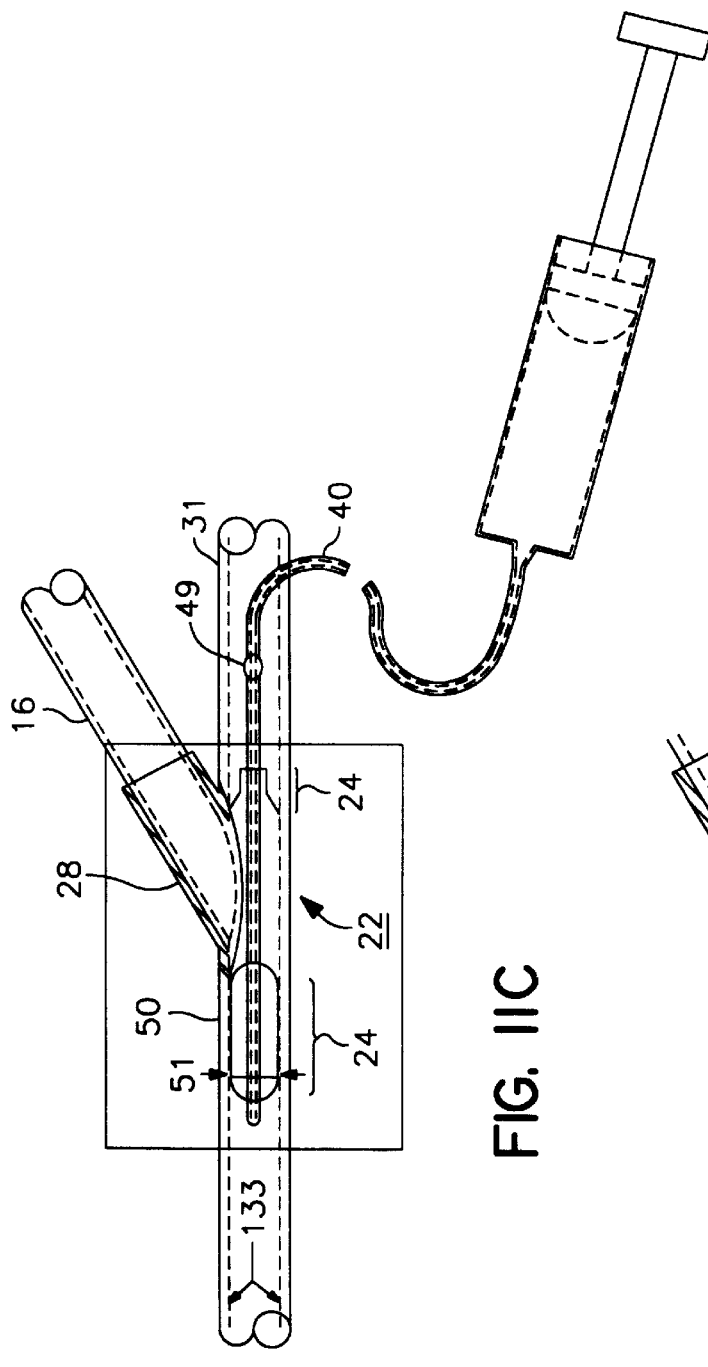
FIG. 11c illustrates a second step of installing the embodiment of the present invention shown in FIGS. 11a and 11b.

The method of installing the distensible junction segment 22 of the present invention is described below and illustrated in FIGS. 11a through 11d. Essentially, the junction segment 22 is positioned within a blood vessel through an incision and then the distensible segments 24 of the junction segment 22 are expanded to form a fluid tight seal against the luminal wall of the blood vessel. As has been explained, the distensible segments 24 are constructed so that they can be relatively easily installed in a blood vessel in a contracted state comprising first dimension 36. This orientation is shown in FIGS. 11a and 11b. Preferably, the first dimension is as small as possible but retains the desired attributes of the present invention. For most AV fistula applications, this will generally comprise a first dimension of about 1 to 5 mm in diameter, with a diameter of 2 to 4 mm being preferred. Once installed, the junction is generally expanded to a diameter of 3 to 8 mm, with a diameter of 3 to 5 mm being most common when the device is implanted in a patient's forearm, and 5 to 7 mm most common when the device is deployed in a patient's upper arm or groin.

FIGS. 11a and 11b illustrate the initial stage of positioning an expansion device 40, such as a balloon catheter assembly, for deployment of the distensible junction segment 22. An expanding member 50 of the expansion device 40 is inserted through a vessel puncture 49 upstream of the distensible segment 24 through the lumen of the distensible junction segment 22. Particular attention should be noted during the positioning of the expansion device 40. The expanding member 50 of the expansion device 40 should not be located external of the distensible segments 24 during the first expansion. Locating the expanding member 50 of the expansion device 40 external of the distensible segments 24 may result in substantial retraction and shortening of the distensible junction segment 22 and/or damage to the host blood vessel.

Figure 11D:
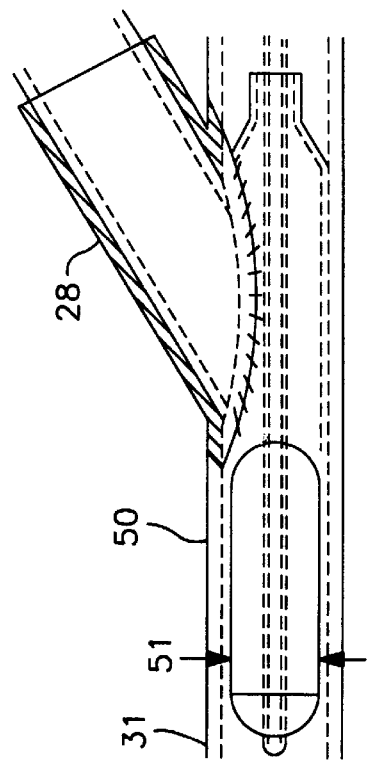
FIG. 11d is a detailed enlargement of the boxed portion of FIG. 11c.

FIGS. 11c and 11d illustrate the final deployment positioning and expansion of the expanding member 50 located at the proximal distensible segment 24. The deployment procedure results in a tight seal between the enlarged distensible segment 24 and the luminal surface 133 of the blood vessel 31. Repeating these procedures for the distal distensible segment 24 completes the deployment of the distensible junction segment 22.

The final enlarged dimension 51 illustrated in FIGS. 11c and 11d will vary depending upon the particular dimensions and conditions of the blood vessel 31. The final dimension should be equivalent to a dimension that provides an adequate seal without substantial damage to the blood vessel 31.

Figure 12A:
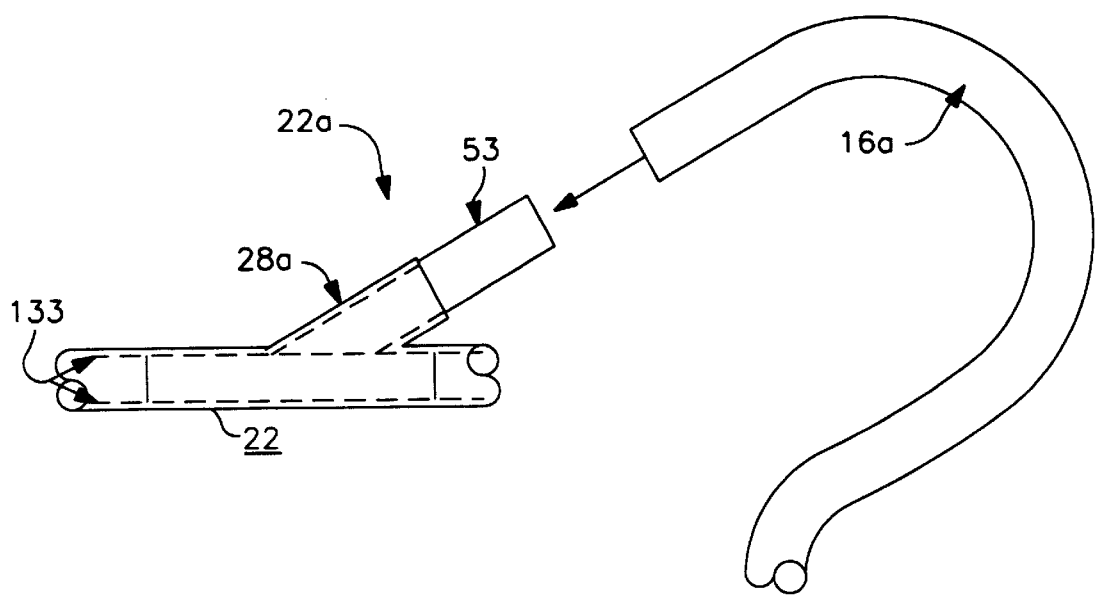
FIGS. 12a and 12b illustrate an additional embodiment in which the junction of the present invention is an intraluminal connector to a blood conduit that may be an autogenous vein, an autogenous artery, or a prosthetic graft.
Figure 12B:
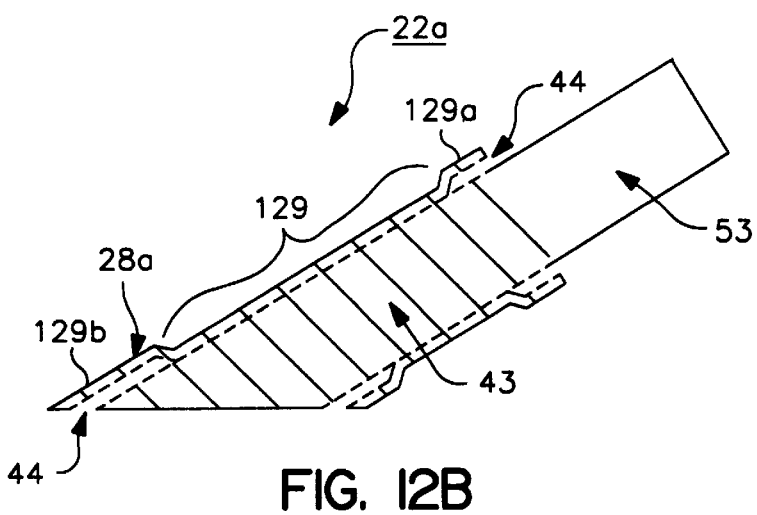

FIGS. 12a and 12b illustrate an additional embodiment of the present invention which provides means to attach a junction to either an autogenous blood vessel (i.e., vein or artery) or a prosthetic graft to form blood conduit 16a. As is shown in FIG. 12a, the connector conduit 22a in this instance comprises a short distensible tube segment 53 and a dual cuff assembly 28a. FIG. 12b is a detailed drawing of the distensible tube segment 53 of FIG. 12a. The dual cuff assembly 28a incorporates distal segment 129a and proximal segment 129b of the connector conduit 22a, which are non-adhered to the short distensible tube segment 53, in order to provide an attachment means to the distensible junction segment 22 and the conduit 16a. Segment 129 is adhered or otherwise firmly attached to distensible tube material 53. In the embodiment shown, the attachment of the connector conduit 22a to the distensible junction segment 26 may be accomplished as detailed previously.

The attachment of the connector conduit 22a to the conduit 16a may be accomplished as follows. The conduit 16a is positioned over the exposed distensible tube segment 53 adjacent to the non-adhered distal segment 129a of the cuff. The conduit 16a is attached to the distal segment 129a of the dual cuff assembly 28a with suture. Subsequently, an expansion device, such as a balloon catheter, is inserted through the lumen of the conduit 16a and positioned to expand the distensible tube material 53. The deployment positioning and expansion technique is explained and described with regard to FIGS. 11a through 11d. In essence, this embodiment provides the surgeon the option of using this invention with synthetic or autogenous blood conduits.

Figure 13:
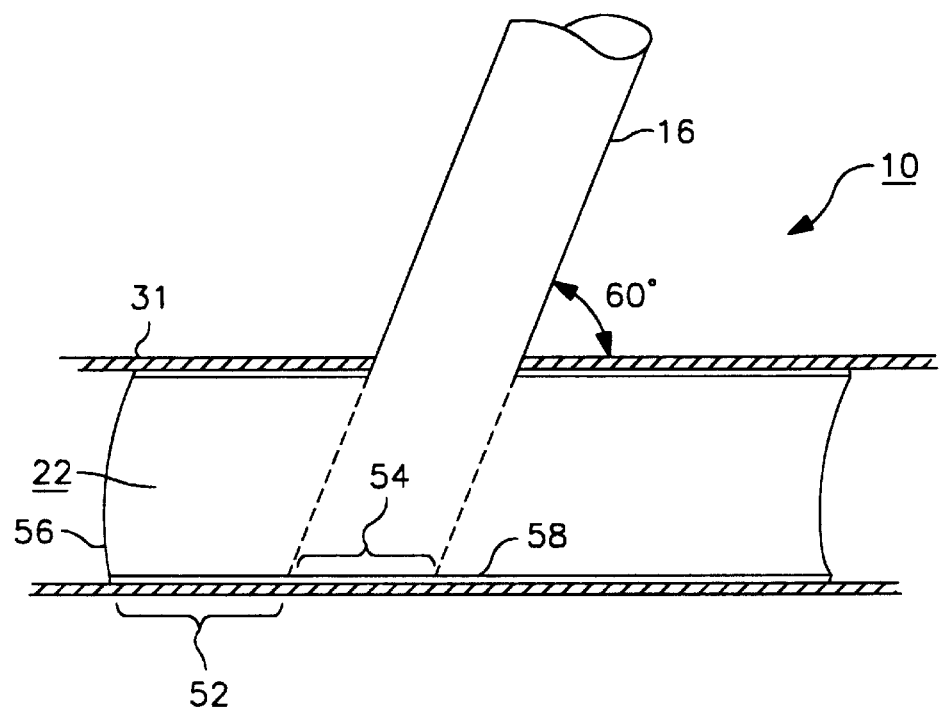
FIG. 13 is a cross-section view of the junction segment of a device of the present invention shown mounted within a blood vessel, having approximately a 60 degree angle of attack, wherein, for clarity, the preferred cuff is not shown.
Figure 14:
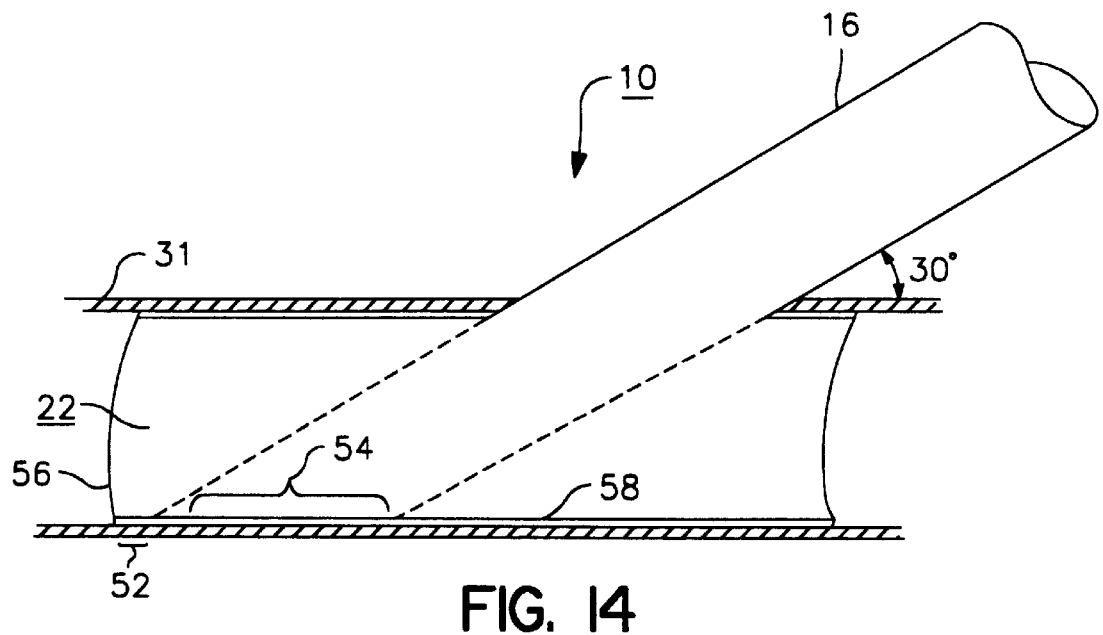
FIG. 14 is a cross-section view of the junction segment of a device of the present invention shown mounted within a blood vessel, having approximately a 30 degree angle of attack, wherein, for clarity, the preferred cuff is not shown.

It is believed that one important aspect of the device of the present invention is its ability to protect the blood vessel wall from direct impact of fluid exiting the blood conduit. Successful protection of the blood vessel wall is believed to be a function of at least two properties of the device of the present invention: controlled "angle of attack," and "impact isolation distance." These two aspects of the present invention are illustrated in FIGS. 13 and 14 and are defined below. For clarity, cuff 28 is not shown in FIGS. 13 and 14.

"Angle of attack" is a function of the angle of attachment of the blood conduit 16 and the junction segment 22 of the present invention. As was previously noted, it is preferred that the blood conduit is attached to the junction at an angle of approximately 10 to 90 degrees off the longitudinal axis of the distensible junction segment, with a preferred angle being between 15 and 45 degrees. Most preferable are angles 25 to 35 degrees off the longitudinal axis of the distensible junction segment, i.e., around 30 degrees. This angle of attachment corresponds to the angle at which fluid flow entering the junction from the blood conduit will impact, or impinge, the junction wall. In this regard, it is desirable to establish an angle of attack that will promote relatively smooth (i.e., relatively non-turbulent or "laminar") flow in the transition between the blood conduit and the blood vessel.

By way of example, FIG. 13 illustrates a blood conduit 16 and distensible junction 22 having about a 60 degree angle of attack; FIG. 14 illustrates a blood conduit 16 and distensible junction 22 having about a 30 degree angle of attack.

In order to avoid stimulating excess cellular growth or migration at the junction site, it is believed important to provide a buffer zone separating the area within the junction 22 receiving the main impact of fluid flow from the blood conduit from the natural vessel tissue. In other words, the prosthetic material of the junction 22 should be positioned to absorb most or all of the impact of the intersecting fluid stream—thus isolating the natural blood vessel 31 from the physical impact and turbulence of the merging fluid stream. This buffer zone is referred to herein as an "impact isolation distance" and is illustrated in FIGS. 13 and 14 as segments 52.

It is believed that the impact isolation distance 52 (i.e., the distance between the primary impact area 54 of the junction receiving the majority of the fluid impact from the blood conduit, and the downstream edge 56 of the distensible junction 22) should be about 3 to 30 mm in length. Preferably, the isolation distance is about 5 to 15 mm in length, with a distance of 7–12 mm being more preferable and a distance of around 10 mm believed to be most preferable. For simplicity in the present application, as is shown in FIGS. 13 and 14, the "primary impact area" 54 can be approximated by drawing straight lines from the periphery of the blood conduit 16 to opposite wall of the junction segment 58. It should be appreciated, however, that the exact location of greatest impact will shift given the relative velocity and force of the two intersecting fluid streams (i.e., the speed and strength of merging fluid stream exiting the blood conduit 16 and the speed and strength of the fluid stream passing through the natural vessel 31).

The impact isolation distance is believed to provide at least two important benefits. First, by shielding the host tissue from direct fluid impact, cellular response to injury is reduced or eliminated. Second, again by shielding the host tissue, fluid flow shear is isolated at the primary impact zone 54, thus avoiding stripping of cells from the host tissue. In both these regards, the primary impact area 54 should comprise a continuous layer of material that both shields blood vessel tissue from direct fluid impact and provides a barrier to cellular growth into the junction in the region of primary impact.

It should be evident from this discussion and review of FIGS. 13 and 14 that the smaller the angle of attachment (i.e., the smaller the angle off the longitudinal axis of the distensible junction segment), the further downstream the primary impact area will be located from the blood conduit attachment site. Accordingly, the downstream length of the junction should be increased as the attachment angle is increased in the device of the present invention.

The device of the present invention may be readily modified to provide a variety of other benefits. For instance, the junction device may be constructed in a number of different shapes and sizes to address specific needs. FIG. 15 illustrates a junction 60 having a Y-shape for use in a side-by-side vascular application 62, where one branch of the natural blood vessel has been excluded. Similarly, as is shown in FIG. 16, a junction 64 can be provided in an X-shape, again for attachment in a side-by-side application whereby the blood vessel branch is not excluded. A cuff 66 may be provided to assist in sealing and anchoring this device in place. A junction device of this configuration is such as might be used to construct a Cimino-Brescia autogenous fistula in a patient.

There may also be benefits to providing a junction 22 of the present invention on the upstream side of a shunt. One embodiment of such a device is shown in FIG. 17, having two junctions 22a, 22b on the blood conduit 16.

Figure 18:
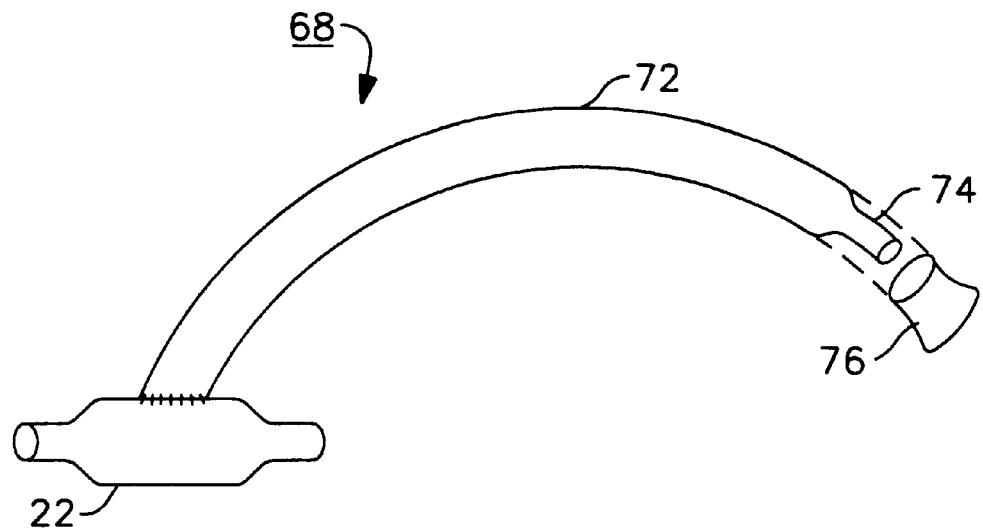
FIG. 18 is a side elevation view of another embodiment of a device of the present invention, having a junction mounted on the first end of a blood conduit and an intraluminal connector on the second end.

For either upstream or downstream applications, a separate junction device 68 may be provided that allows for ready attachment to a blood conduit, either natural or artificial. As is shown in FIG. 18, a separate junction device 68 may comprise a tube 72, as previously described with respect to junction 22, with a further expandable fitting 74 thereon adapted to be inserted within a conduit (either natural or artificial) and expanded in place. Preferably, the expandable fitting is constructed from the same material and the same manner as previously described with respect to the junction 22. A removable cuff 76 may also be provided with this device to aid in attachment between the blood vessel and the conduit.

Figure 19:
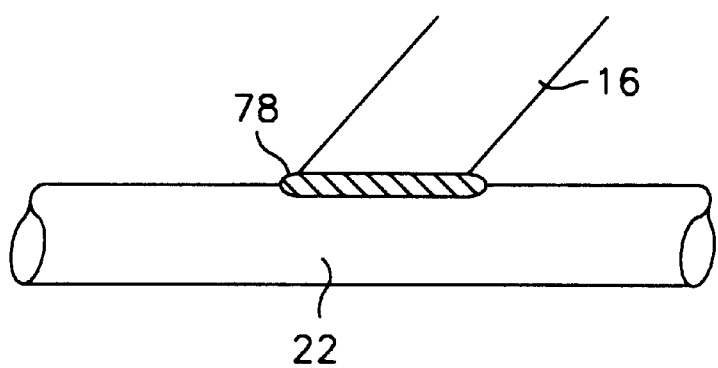
FIG. 19 is a side elevation view of another embodiment of a cuff of the present invention.

As shown in FIG. 19, the cuff may alternatively be made by adding a low profile band 78 of material along the juncture of the blood conduit 16 and the distensible junction segment 22 through which a surgeon may suture, staple, or otherwise attach the cut edges of the blood vessel to facilitate anchoring the device and creating a blood tight seal without penetrating into the blood flow surface of the device. The band 78 may be constructed from a variety of materials, such as polyethylene terephthalate mesh, PTFE tubing or beading, silicone beading, or similar material that will retain an anchorage means.

It should be appreciated from review of the above description that a variety of other modifications and adaptations may be incorporated into the device of the present invention without departing from the spirit thereof.

Without intending to limit the scope of the present invention, the following examples illustrate how the present invention may be made and used:

EXAMPLE 1

One embodiment of an AV access blood conduit and junction of the present invention may be manufactured in the following manner.

A tube is made in accordance with the process steps outlined in the flow chart of FIG. 9. A substrate tube of step 1 is made in accordance with the teaching of U.S. Pat. No. 3,953,566 to have the following properties: a 2.2 mm inner diameter, a 0.60 mm wall thickness, a fibril length of about 22 $\mu$m, a density of about 0.3 g/cm$^3$, and about was 86% porous by bulk volume. The tube is subjected to at least 380° C. for about 1 minute, exceeding the crystalline melt point of PTFE, in order to provide dimensional stability. The tube is placed over a 2.6 mm outer diameter INCONEL® (Huntington Alloys, Inc.) mandrel and compressed longitudinally to about 20% of its initial length (step 2). The tube on the mandrel is then placed for 42 seconds in an air convection oven set at 380° C. as per step 3.

Upon removal from the oven and cooling, with the tube still compressed longitudinally and secured on the mandrel, the tube is laser treated using model 2010, 20 W $CO_2$ laser with a 6.35 mm focal length lens (Applied Laser Technology, Inc., Scottsdale, Ariz.). A clamping device and a motor installed within the laser chamber enables the tube to be rotated under the laser beam. The laser treatment employs a laser beam striking the surface of the tube, creating rings around the circumference of specific sites along the length of the tube. The laser is operated in the proportional pulse mode with a pulse width of 300, and a pulse rate of 39999, while the graft is rotated at 600 revolutions per minute. The top of the graft is situated 9.4 cm below a reflecting mirror. The beam is set up to treat 0.7 mm wide regions with 1.6 mm wide gaps between the treated regions. This process is performed in accordance with step 4.

Per step 5, the tube is removed from the mandrel and extended under tension as per step 6 until the 1.6 mm wide gaps are increased in width to about 4.0 mm. The graft is reloaded onto the 2.6 mm outer diameter mandrel (per step 7) with its length extended to preserve the widths of the treated regions and the gaps.

As shown by step 8, 2.5 cm wide porous PTFE film made in accordance with U.S. Pat. No. 3,953,566 is used with the following properties: a fibril length of about 50 $\mu$m, a density of about 0.3 g/cm$^3$, a thickness of 0.01 mm, and is 86% porous by bulk volume. The film is wrapped helically around a 10 mm outer diameter INCONEL mandrel utilizing a 6.4 mm pitch. The film is helically applied in two passes of opposing direction. The film tube is then heated per step 9 for 11 minutes in an air convection oven set at 380° C. Next, the film tube is removed from the mandrel (step 10). The film tube is placed coaxially over the porous PTFE tube of step 7. Tension is applied to the film tube in the longitudinal direction until the film tube fits snugly over the porous PTFE tube. Next, the film tube cover PTFE tube is longitudinally restrained, thereby completing step 11. Next the mandrel containing the film tube and porous PTFE tube is placed for 9 minutes into an oven set at 380° C. in order to bond the film tube to the PTFE tube, per step 12.

The composite tube is then removed from the mandrel (step 13) and stretched in the radial direction by first pushing it onto the small end of a tapered INCONEL mandrel having an outer diameter of 4 mm on one end and 7 mm at the other and then pushing it onto the 6 mm section of the mandrel. A short portion of the tube is left unstretched in order to facilitate later drawing through a die (step 14). The tube is maintained in a longitudinally compressed state throughout this step.

The composite tube is next heat treated to better provide resistance to recoil (step 15). The composite is placed for 3 minutes into an air convection oven set at 380° C. The composite tube is then removed from the mandrel (step 16) and subsequently pulled through a 3.8 cm long tapered die with an inner diameter of 8 mm at one end and inner diameter of 4 mm at the other end. Upon exiting the die, the composite tube is pulled inside a 3.8 mm inner diameter perfluoro alkoxy resin (PFA) tube (step 17) in order to longitudinally and radially restrain the tube. The tube should be devoid of wrinkles. The graft within the PFA tube is placed into an air convection oven set at 200° C. for a period of 3 minutes (step 18). The composite graft is subsequently removed from the PFA tube (step 19) and loaded onto a mandrel having a 2.6 mm outer diameter (step 20). The composite tube is longitudinally compressed to approximately 75% of its original length and then restrained so it can not lengthen (step 21). The subsequent heat treatment is performed for 10 minutes in an oven set at 200° C. to serve to reduce the amount of foreshortening of the tube during later circumferential distension. In the last step, step 23, the composite distensible tube is removed from the mandrel.

A 75 mm length of the finished distensible tube is placed inside two stainless steel end sleeves with a gap of about 39 mm. An 8 mm outer diameter by 4 cm long ballooning catheter (e.g., a Bard® TruTrac PTA Balloon Dilatation Catheter, Bard Radiology Division, C.R. Bard, Inc., Covington, Ga.) is inserted into the distensible material with the expanding portion of the ballooning catheter extending beyond the 39 mm gap. A stainless steel sleeve is positioned over the 39 mm gap and the assembly placed into a supporting member.

The ballooning catheter is inflated to 12 atmospheres for 60 seconds, deflated for 60 seconds, re-inflated to 12 atmospheres for 60 seconds, deflated, then removed from the fixture and supporting member.

The distensible junction segment with the enlarged mid-section is placed on a stainless steel laser mandrel and the enlarged mid-section laser cut to create an access incision corresponding to the geometry of the end of the blood conduit. Suture holes are laser generated around the access incision at approximately 1 mm spacing and 1 mm bite.

The cuff and blood conduit are created in the following manner. A 6 mm stainless steel mandrel is inserted inside a commercially available expanded PTFE vascular graft; in this instance, the graft is a straight, standard wall GORE-TEX® vascular graft having an internal diameter of 6 mm available from W. L. Gore & Associates, Inc., Flagstaff, Ariz. The graft is secured to the mandrel by wrapping silver plated copper wire around the graft and mandrel and twisting the ends to prevent the graft from moving.

A stainless steel cuff sleeve is positioned over both ends of the vascular graft. An expanded PTFE tube, having an internal diameter of 6 mm, is stretched over the stainless steel cuff sleeve, extending approximately 13 mm onto the vascular graft.

A porous PTFE film, as previously described is wrapped over the expanded PTFE tube, extending approximately 13 mm beyond its end onto the vascular graft. The PTFE film comprises primarily fibrils that are oriented substantially in the longitudinal direction of the film, resulting in the fibrils being oriented substantially in the circumferential direction around the outer surface of the tube, thereby reinforcing and adhering the cuff to the blood conduit. The porous expanded PTFE film is helically wrapped in a single direction with respect to the longitudinal axis of the expanded PTFE tube.

The blood conduit with cuff assembly is placed in an air convection oven for 15 minutes at 370° C., allowed to cooled, then the mandrel and cuff sleeve are removed.

A stainless steel laser mandrel is inserted inside the blood conduit with cuff assembly. The blood conduit with cuff assembly is laser cut at a 30 degree angle with suture holes generated around the cut edge at approximately 1 mm spacing and 1 mm distance from the cut edge. The holes correspond to the suture hole locations on the mid-section of the distensible junction segment.

The junction and conduit subassemblies are attached in the following manner. The cuff material is folded back to expose the blood conduit and suture holes. The blood conduit and mid-segment of the distensible junction segment are laced together using an over-and-over stitch with a suture. In this instance, a GORE-TEX® CV-5 suture (available from W. L. Gore & Associates, Flagstaff, Ariz.) is used. Each suture is tensioned using approximately 380 gram hanging weight prior to knotting.

The seam line and suture holes are sealed using Silicone Med-1137 silicone thinned with N-heptane J338-3 in the ratio of 10:1 by weight. The silicone and heptane are mixed in the following manner. Silicone, 200 grams±1 g, is placed inside a glass bottle. N-heptane, 20 g±1 g, is added to the bottle, which is immediately sealed by tightly placing a cap on the glass bottle. The bottle is placed on a set of slowly rotating horizontal rollers for 24 hours.

After six silicone applications to the seam line, the silicone is allowed to cure for about 24 hours under ambient conditions. Finally, the device is steam sterilized prior to implantation.

EXAMPLE 2

An AV access blood conduit and junction made in accordance with Example 1 is installed in the following manner.

In an anesthetized and heparinized (100 U/kg) canine, the femoral artery and femoral vein are exposed using standard surgical technique. The femoral vein is occluded proximally and distally with vascular clamps. A venotomy, approximately the length of the manufactured anastomosis joining the blood conduit and junction, is created in the vein. The distensible junction segment is inserted into the vein through the venotomy. The cuff is attached to the venotomy using GORE-TEX® Suture, CV-7 with a TT-9 needle to anchor the device and to assist in forming a fluid tight seal between the distensible junction segment and the blood vessel. A small venipuncture is created in the vein about 1 cm upstream from the end of the distensible junction segment and a ballooning catheter is inserted into the distensible junction segment. The balloon is inflated to enlarge the distensible junction segment, thereby forming a fluid tight seal between the distensible junction segment and the blood vessel luminal surface. The venipuncture is sutured closed.

The AV blood conduit is tunneled subcutaneously in a loop configuration using standard surgical technique. The free end of the blood conduit is trimmed to an appropriate length and angle. The femoral artery is clamped proximally and distally so that an arteriotomy can be created. The free end of the blood conduit is attached to the artery in an end-to-side anastomosis using GORE-TEX Suture, CV-7 with a TT-9 needle. The vascular clamps are removed, thereby establishing flow through the blood conduit and the junction segment. Hemostasis at the conventionally sewn anastomosis is established.

No leakage of blood is observed between the blood vessel and the distensible junction segment because the fit between the two components is tight enough to prevent leakage. The skin incision is closed using conventional surgical techniques.

EXAMPLE 3

An AV access blood conduit and junction made in accordance with Example 1 is alternatively installed in the following manner.

The graft and junction is installed in a canine as described in Example 2 Instead of inserting a ballooning catheter into the device through a venipuncture, a flexible guidewire (Terumo Glidewire, 0.035 in. O.D. with angled tip, available from Medi-tech, Watertown, Mass.) is threaded through the blood conduit to the distensible junction segment. The guidewire is directed into the upstream portion of the distensible junction segment using digital guidance. With the guidewire in place, the same ballooning catheter used in Example 2 is passed along the guidewire into the distensible junction segment, where the balloon is inflated to distend the distensible junction segment. The ballooning catheter is removed from the distensible junction segment and the guidewire repositioned into the remaining non-distended portion of the distensible junction segment. The catheter is advanced along the guidewire, positioned appropriately, and the balloon inflated to distend the distensible junction segment.

The ballooning catheter and guidewire are removed and the remaining end-to-side anastomsis at the artery is created. The vascular clamps are removed, thereby establishing flow through the graft conduit and junction device.

EXAMPLE 4

Each of eight canines receive implants of an AV blood conduit and distensible junction manufactured as described in Example 1 (the test graft). Installation of these devices into one hind limb of each animal is conducted as described in Example 2. In the contralateral hind limb, each animal receives an AV access blood conduit without a junction of the present invention (the control graft). The control blood conduit is implanted using standard end-to-side suture technique on both the arterial and the venous anastomoses. Surgical incisions are closed routinely and the animals allowed to recover from anesthesia.

At about 90 days post-operatively, all control grafts in seven of the canines are retrieved, each of the control grafts showing significant hyperplasia at the suture line of the venous anastomoses. There is a ridge of tissue along the suture line, and significant thickening of the vein in the primary impact zone region. This thickening extends a short distance downstream from the impact zone. All control grafts retrieved at 90 days have more than 90% of the lumen stenosed.

The test grafts retrieved at 90 days have slight tissue growth at both ends of the distensible intraluminal segment, which extend a few millimeters onto the distensible intraluminal segment. No tissue is present along the manufactured suture line. These grafts retained more than 90% of the original flow cross sectional area.

The remaining animal is maintained until both the test and the control graft occlude. The control graft is diagnosed to be totally occluded at about 100 days. The test graft occludes at about 155 days, an extension of primary patency of about 1.5 times.

This experiment demonstrates that the inventive features of the device of the present invention extend significantly the primary patency of AV access grafts by mitigating the factor or factors responsible for inducing anastomotic stenoses.

EXAMPLE 5

Figure 20:
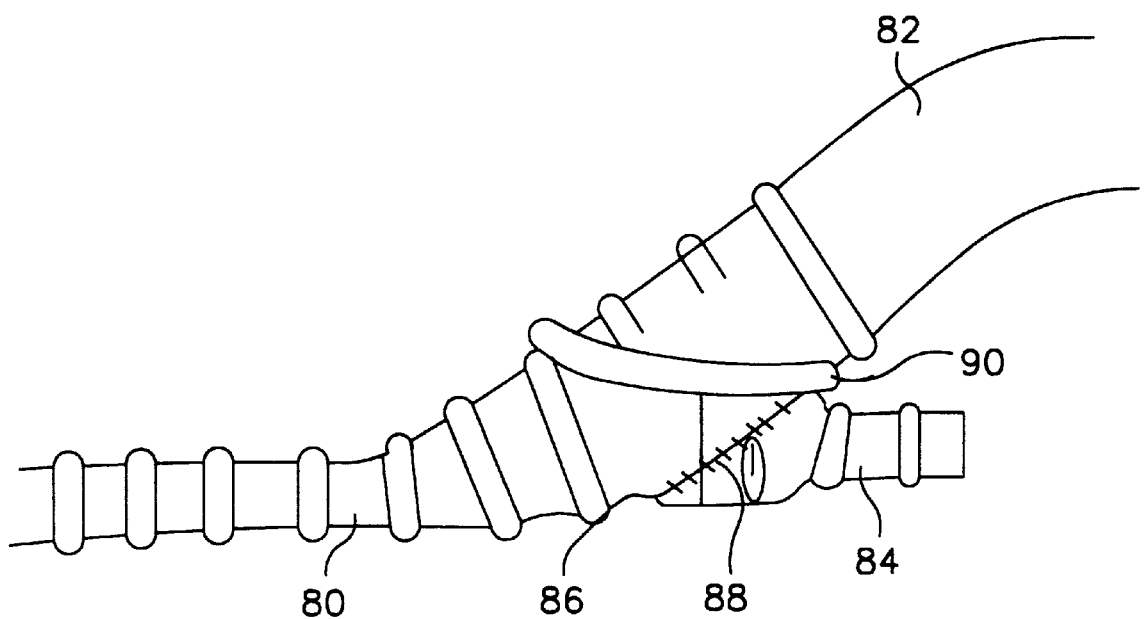
FIG. 20 is a side elevation view of another embodiment of a device of the present invention.

As is illustrated is FIG. 20, yet another embodiment of the present invention is described as follows. A tube 80 made in accordance with Example 1 is used. The tube 80 may be continuous with a non-expandable segment 82 or the non-expandable segment 82 may comprise a separate tube that is attached to tube 80. The non-expandable segment 82 will comprise the upstream junction for this device when installed.

A second expandable tube 84 made in accordance with Example 1 is then attached to tube 80 through use of sutures 86 and/or other attachment means (such as adhesives, staples, etc.). A seam line 88 is then presented between the two tubes 80, 84, which should be sealed to prevent leakage.

Constructed in this manner, tube 80 and tube 84 form the distensible junction of the present invention. A cuff or sewing ring 90, as previously described, may be provided to aid in the attachment of this embodiment.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A junction device having an interior and adapted for implantation within a blood vessel to direct blood flow between two streams of blood, the device comprising a connector having at least three legs, the connector being adapted to merge blood flow into, or separate blood flow from, a continuous blood vessel;

wherein the first and second legs are adapted to be inserted into the continuous blood vessel in a contracted state and then be enlarged in place to form a tight fit within the continuous blood vessel so as to direct blood flow through the interior of the junction device; and wherein the third leg is adapted to exit the continuous blood vessel through an opening formed in the blood vessel to connect a second stream of blood into or from the continuous blood vessel; and means surrounding the third leg to permit the opening in the blood vessel to be sealed around the third leg without requiring formation of punctures through the junction device into the interior.

2. The junction device of claim 1 wherein the third leg comprises a conduit for fluid connection between the continuous blood vessel and a second blood vessel.

3. The junction device of claim 1 wherein the means surrounding the third leg to permit the opening in the blood vessel to be sealed comprises a cuff sealed to the third leg that is adapted to be affixed around the opening in the continuous blood vessel.

4. The junction device of claim 1 wherein the means surrounding the third leg to permit the opening in the blood vessel to be sealed comprises a ring of material attached to the third leg adapted to receive anchoring sutures placed around the opening in the continuous blood vessel without requiring sutures to penetrate through the junction device into the interior.

5. The junction device of claim 1 wherein the third leg is attached to the first and second legs at an angle; and the angle between a straight line through the third leg parallel to a longitudinal axis of the third leg and a straight line through the first and second legs parallel to a longitudinal axis of the first and second legs is at least 15 degrees.

6. The junction device of claim 1 where device has an impact isolation distance of at least 10 mm.

7. The junction device of claim 1 wherein the third leg is attached to the device by sutures.

8. The junction device of claim 7 wherein a sealant is applied around the sutures to prevent leakage through the device.

9. The junction device of claim 1 wherein the first and second legs consist of a fluoropolymer material that is self-supporting in an enlarged state to form a tight fit within the blood vessel without the need for separate anchoring means within the blood vessel.

10. A junction device adapted for implantation within a blood vessel to direct blood flow between a first stream of blood and a second stream of blood, the device comprising a connector having an interior and being adapted to be inserted within a blood vessel, and a conduit in fluid communication with the connector to connect the first and second streams of blood;

the connector being adapted to be inserted into the blood vessel in a contracted state and then be enlarged in place to form a tight fit within the blood vessel so as to direct blood flow through the interior of the junction device;

the connector being adapted to exit the blood vessel through an opening formed in the blood vessel to connect the second stream of blood with the blood vessel;

means attached to the conduit to permit the opening in the blood vessel to be sealed around the conduit without requiring formation of punctures through the junction device into the interior; and wherein at least the connector consist of fluoropolymer material that is self-supporting in an enlarged state to form a tight fit within the blood vessel without the need for separate anchoring means within the blood vessel, the connector undergoing less than a 10% foreshortening in overall length when it is enlarged from the contracted state to the enlarged state.

11. The junction device of claim 10 wherein the connector undergoes less than a 8% foreshortening in overall length when it is enlarged from the contracted state to the enlarged state.

12. The junction device of claim 10 wherein the connector undergoes less than a 5% foreshortening in overall length when it is enlarged from the contracted state to the enlarged state.

13. The junction device of claim 10 wherein the fluoropolymer material comprises polytetrafluoroethylene.

14. The junction device of claim 10 wherein the means attached to the conduit to permit the opening in the blood vessel to be sealed comprises a cuff attached to the conduit that is adapted to be affixed around the opening in the blood vessel.

15. The junction device of claim 10 wherein the means attached to the conduit to permit the opening in the blood vessel to be sealed comprises a ring of material attached to the conduit adapted to receive anchoring sutures placed around the opening in the blood vessel without requiring sutures to penetrate through the junction device into the interior.

16. The junction device of claim 10 wherein the connector comprises first and second legs adapted to be inserted within a continuous blood vessel;

the conduit is attached to the first and second legs at an angle; and the angle between a straight line through the conduit parallel to a longitudinal axis of the conduit and a straight line through the first and second legs parallel to a longitudinal axis of the first and second legs is at least 15 degrees.

17. The junction device of claim 10 where device has an impact isolation distance of at least 10 mm.

18. The junction device of claim 10 wherein the conduit is attached to the connector by sutures.

19. The junction device of claim 18 wherein a sealant is applied around the sutures to prevent leakage through the device.

20. The junction device of claim 13 wherein the polytetrafluoroethylene comprises a porous polytetrafluoroethylene.

21. The junction device of claim 13 wherein the polytetrafluoroethylene comprises an expanded polytetrafluoroethylene.

22. A junction device for connecting a first blood stream and a second blood stream, the device having an interior through which blood flows, the device comprising a connector adapted to be inserted within a blood vessel through which the first blood stream flows, and a conduit in fluid communication with the connector adapted to merge blood flow from the second blood stream into the first blood stream;

the connector adapted to be inserted into the blood vessel in a contracted state and then be enlarged in place to form a tight fit within the blood vessel so as to direct blood flow through the interior of the junction device; and the connector being adapted to exit the continuous blood vessel through an opening formed in the blood vessel to connect to the second blood stream;

the conduit is attached to the connector at an angle;

the junction device includes a primary impact area within the connector comprising an area on an interior wall of the connector opposite the conduit;

wherein the junction device is constructed from a continuous material that completely covers the blood vessel at least over the primary impact area; and wherein the junction device includes means to seal the opening in the blood vessel around the conduit without sutures penetrating into the interior of the junction device.

23. The junction device of claim 22 wherein the conduit includes an inner wall and a longitudinal axis; and the primary impact area is a portion of the device defined by drawing a series of straight lines from the conduit along the inner wall parallel to the longitudinal axis of the conduit to the interior wall of the connector.

24. The junction device of claim 22 wherein the junction device includes an isolation distance between the primary impact area and the end of the connector; and the isolation distance is between about 3 and 30 mm.

25. The junction device of claim 24 wherein the isolation distance is between about 5 and 15 mm.

26. The junction device of claim 24 wherein the isolation distance is between about 8 and 12 mm.

27. The junction device of claim 22 wherein the connector comprises first and second legs adapted to be inserted within a continuous blood vessel;

the angle of attachment between the first and second legs and the conduit is approximately between 10 and 90 degrees off a longitudinal axis drawn through the first and second legs.

28. The junction device of claim 27 wherein the angle of attachment is approximately between 15 and 45 degrees off the longitudinal axis drawn through the first and second legs.

29. The junction device of claim 27 wherein the angle of attachment is approximately between 25 and 35 degrees off the longitudinal axis drawn through the first and second legs.

30. The junction device of claim 22 wherein the entire junction device comprises continuous fluoropolymer material.

31. The junction device of claim 22 wherein at least the connector consist of fluoropolymer material.

32. The junction device of claim 22 wherein the means to seal the opening in the blood vessel comprises a cuff attached to the conduit that is adapted to be affixed around the opening in the blood vessel.

33. The junction device of claim 22 wherein the means to seal the opening in the blood vessel comprises a ring of material attached to the conduit adapted to receive anchoring sutures placed around the opening in the blood vessel without requiring sutures to penetrate through the junction device into its interior.

34. The junction device of claim 22 wherein the device comprises a material resistant to tissue in-growth through the device into its interior.

35. The junction device of claim 22 that further comprises the connector being adapted to undergo less than a 10% foreshortening in overall length when it is enlarged from the contracted state to an enlarged state.

36. The junction device of claim 22 wherein at least the connector comprises a fluoropolymer material that is self-supporting in an enlarged state to form a tight fit within the blood vessel.

37. A junction device having an interior and adapted for implantation within a blood vessel, the device comprising
   a connector adapted to be inserted into the blood vessel in a contracted state and then be enlarged in place to form a tight fit within the blood vessel so as to direct blood flow through the interior of the junction device;
   a conduit attached to the connector, the conduit adapted to exit the blood vessel through an opening formed in the blood vessel to connect to a stream of blood; and
   means surrounding the conduit to permit the opening in the blood vessel to be sealed around the conduit without requiring formation of punctures through the junction device into the interior.

38. The junction device of claim 37 wherein the means surrounding the conduit to permit the opening in the blood vessel to be sealed comprises a cuff attached to the conduit that is adapted to be affixed around the opening in the blood vessel.

39. The junction device of claim 37 wherein the means surrounding the conduit to permit the opening in the blood vessel to be sealed comprises a ring of material attached to the conduit adapted to receive anchoring sutures placed around the opening in the blood vessel without requiring sutures to penetrate through the junction device into the interior.

40. The junction device of claim 37 where device has an impact isolation distance of at least 10 mm.

41. The junction device of claim 37 wherein the conduit is attached to the connector by sutures.

42. The junction device of claim 41 wherein a sealant is applied around the sutures to prevent leakage through the device.

43. The junction device of claim 37 wherein the connector comprises a fluoropolymer material that is self-supporting in an enlarged state to form a tight fit within the blood vessel without the need for separate anchoring means within the blood vessel.

44. The junction device of claim 43 wherein the connector undergoes less than a 8% foreshortening in overall length when it is enlarged from the contracted state to the enlarged state.

45. The junction device of claim 43 wherein the connector undergoes less than a 5% foreshortening in overall length when it is enlarged from the contracted state to the enlarged state.

46. The junction device of claim 43 wherein the fluoropolymer material comprises polytetrafluoroethylene.

47. The junction device of claim 43 wherein the polytetrafluoroethylene comprises a porous polytetrafluoroethylene.

48. The junction device of claim 43 wherein the polytetrafluoroethylene comprises an expanded polytetrafluoroethylene.

* * * * *